United States Patent
Ohtsuki et al.

(10) Patent No.: US 6,887,920 B2
(45) Date of Patent: May 3, 2005

(54) FILLINGS AND COMPOSITE DENTAL MATERIALS CONTAINING THE FILLINGS

(75) Inventors: Junichi Ohtsuki, Osaka (JP); Hirotaka Kita, Okayama (JP); Koichi Okada, Okayama (JP); Yasujiro Ohara, Okayama (JP)

(73) Assignee: Kuraray Co., Ltd., Kurashiki (JP)

( * ) Notice: Subject to any disclaimer, the term of this patent is extended or adjusted under 35 U.S.C. 154(b) by 296 days.

(21) Appl. No.: 10/168,542

(22) PCT Filed: Nov. 1, 2001

(86) PCT No.: PCT/JP01/09579

§ 371 (c)(1),
(2), (4) Date: Jul. 2, 2002

(87) PCT Pub. No.: WO02/36691

PCT Pub. Date: May 10, 2002

(65) Prior Publication Data

US 2003/0060533 A1 Mar. 27, 2003

(30) Foreign Application Priority Data

Nov. 2, 2000 (JP) .......................................... 2000-335888

(51) Int. Cl.⁷ ............................. A61K 6/08; C08K 3/20; C04B 35/01

(52) U.S. Cl. ...................... 523/116; 523/117; 524/430; 501/2; 501/151; 501/154; 428/402

(58) Field of Search ................................ 523/116, 117; 524/430; 501/2, 151, 154; 428/402

(56) References Cited

U.S. PATENT DOCUMENTS 6,297,181 B1 10/2001 Kunert et al.

FOREIGN PATENT DOCUMENTS

| EP | 129959 | 1/1985 |
|---|---|---|
| EP | 821931 | 2/1998 |
| EP | 0 997 132 | 5/2000 |
| JP | 362123042 A * | 6/1987 |
| JP | 2-258602 | 10/1990 |
| JP | 3-151313 | 6/1991 |
| JP | 5-85915 | 4/1993 |

* cited by examiner

Primary Examiner—Tae H. Yoon
(74) Attorney, Agent, or Firm—Oblon, Spivak, McClelland, Maier & Neustadt, P.C.

(57) ABSTRACT

The present invention provides a filler which has high water resistance and high acid resistance, and high releasing abilities of ions such as fluorine ions, and can maintain high aesthetic appreciation for a long period of time, and a dental composite material comprising the filler, excellent in water resistance, acid resistance, ion releasability and aesthetic appreciation.

13 Claims, 12 Drawing Sheets

FILLINGS AND COMPOSITE DENTAL MATERIALS CONTAINING THE FILLINGS

TECHNICAL FIELD

The present invention relates to a filler (hereinafter also referred to as filler) and a dental composite material comprising the filler. The dental composite material of the present invention is used as composite resins for dental fillers, composite resins for core build-up, crown composite resins, denture base resins, dental adhesive resin cements, dental fissure sealants, dental varnishes or coating agents, dental bonding agents, tooth adhesion primers, dental manicures, materials for root canal filling, and the like.

BACKGROUND ART

In the treatment of dental caries and defects, a dental composite material comprising a resin and an inorganic filler (hereinafter referred to as a composite material in some cases) has been widely used in place of conventional metal materials. Such a composite material is excellent in mechanical strength, aesthetic appreciation, durability, and the like, and the composite material is useful in the morphological restoration of a desired site and as an adhesive for the adhesion of a dental material to teeth.

In recent years, those materials having an additional ion-releasing function, especially fluorine ion-releasing function, to these composite materials have been clinically used. By supplying fluorine ions to the teeth after the restoration, these materials have additional functions of changing hydroxyapatite, which is a main constituent of teeth, to a higher acid-resistant fluoroapatite, thereby increasing the resistance to caries of teeth, accelerating the calcification of mineral components in the saliva and tissue fluids or the like. Therefore, opportunities for the clinical use of these materials for preventing the onset and recurrence of dental caries have been increasing.

As those conventionally used as a filler acting as a fluorine ion-releasing source in these composite materials, there have been known fluorine-containing glass such as fluoroaluminosilicate glass, fluorine-containing organic polymer compounds (Japanese Patent Laid-Open No. Hei 5-85915), fine particles obtained by sublimating the solvent from a metal fluoride solution (Japanese Patent Laid-Open No. Hei 2-258602), and the like. Also, more recently, there has been proposed a metal fluoride having a polysiloxane coating layer on the surface thereof (Japanese Patent Laid-Open No. Hei 10-36116). In this publication, it is disclosed that the composite material comprising the metal fluoride is excellent in mechanical strength and amount of fluorine ions released. This technique is basically thought to be encompassed within the scope of the technique in which the surfaces of metal fluoride particles are treated with a silane-coupling agent.

In a case where a composite material comprising sodium fluoride or fluoroaluminosilicate glass as a filler is filled in a defective site of the tooth and then subjected to finish polishing, fluorine ions are effectively released in an oral cavity upon the contact of these orally exposed particles with water. However, the filler itself, at the same time, is gradually dissolved, resulting in detachment of the filler from the surface of the composite material or generation of voids in the inner portion of the filler, whereby the aesthetic appreciation and the mechanical strength of the composite material are lowered. The fluoroaluminosilicate glass, which is the most frequently used material, is likely to dissolve when the degree of acidity of water to which the glass is exposed is increased, so that dissolution is caused within the changing range of pH in the oral cavity (pH 5 to 7).

On the other hand, the fluorine-containing polymer compound does not cause deterioration of the surface properties or lowering in the mechanical strength of the composite materials as mentioned above. However, since the polymer compound itself has low transparency, the aesthetic appreciation of the composite material is lowered. Also, since the releasing rate of the fluorine ions from the composite material is gradual, the clinical effect would be less likely to be exhibited at an early stage.

When the fluorine ion-releasing source is used as a filler for the composite material, it is important that the composite material has appropriate transparency in order to ensure aesthetic appreciation of the composite material. In order to ensure the aesthetic appreciation of the composite material, it is effective to reduce the difference in visible light refractive indices between an X-ray opaque glass such as fluoroaluminosilicate glass, barium-containing glass, strontium-containing glass or lanthanum-containing glass, which is used as the filler, and the resin constituting the composite material. However, since sodium fluoride, which is often used as a fluorine ion-releasing source, has a drastically low photorefractive index than that of the filler or the polymer compound mentioned above, the transparency of the composite material is lowered when added in large amounts, thereby undesirably worsening the aesthetic appreciation of the composite material.

Also, in the technique using a metal fluoride having a polysiloxane coating layer on the surface thereof disclosed in Japanese Patent Laid-Open No. Hei 10-36116 mentioned above, there are some defects in that the metal fluoride powder used has a large particle size, so that large voids are generated due to the dissolution of the metal fluoride particles in the oral cavity, and that the transparency of the composite material comprising the metal fluoride is lowered.

An object of the present invention is to provide a filler which has high water resistance and high acid resistance, and high releasing abilities of ions such as fluorine ions, and can maintain high aesthetic appreciation for a long period of time, and a dental composite material comprising the filler, excellent in water resistance, acid resistance, ion releasability and aesthetic appreciation.

DISCLOSURE OF INVENTION

The present inventors have made intensive studies for obtaining the filler and the dental composite material comprising the filler satisfying the above-mentioned object. As a result, the present inventors have found that the above-mentioned object can be accomplished by providing a filler comprising a mixture of at least one metal oxide and at least one water-soluble metal salt, in which each of the two components form an independent phase, and the water-soluble metal salt phase comprises a crystal of the water-soluble metal salt having a specified average particle size, and by formulating the filler in a dental composite material. The present invention has been perfected thereby.

Specifically, the gist of the present invention relates to:
(1) a filler comprising at least one metal oxide and at least one water-soluble metal salt, the metal oxide and the water-soluble metal salt each forming an independent phase, characterized in that the water-soluble metal salt phase comprises a crystal of the water-soluble metal salt having an average particle size of from 0.001 to 0.3 μm;
(2) a process for preparing the filler of item (1) above, comprising mixing a metal oxide and/or a hydrolyzed product of a hydrolysable organometallic compound with an aqueous solution of a water-soluble metal salt, and drying the resulting mixture; and
(3) a dental composite material comprising the filler (a) of item (1) above, a polymerizable monomer (b) and a polymerization initiator (c).

BEST MODE FOR CARRYING OUT THE INVENTION

Figure 1:
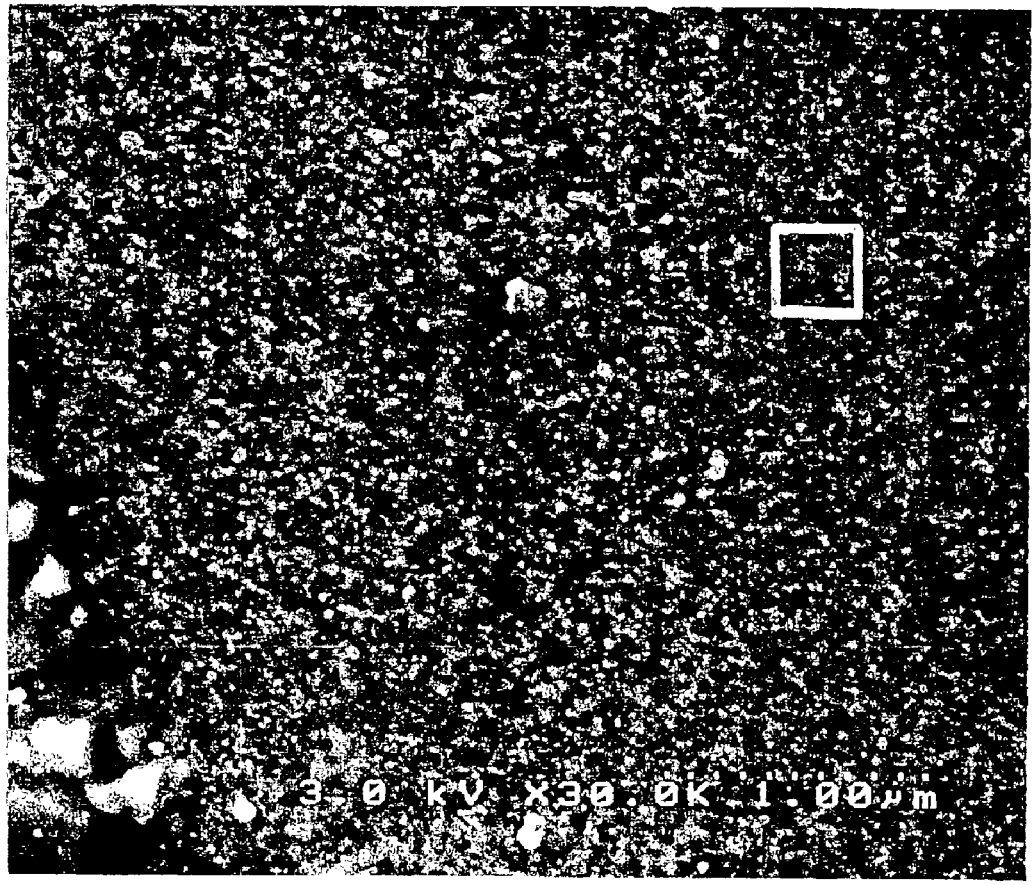
FIG. 1 is an electron microphotograph of an ion-releasable filler in Example 1.
Figure 2:
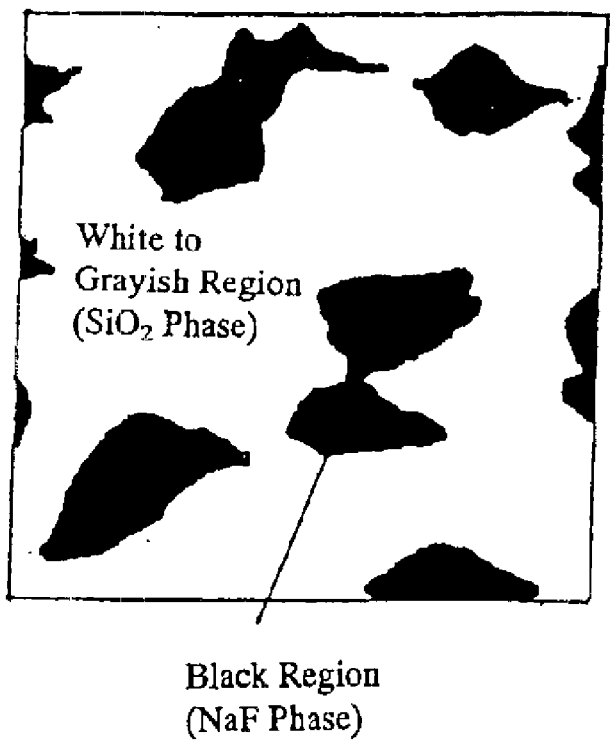
FIG. 2 is an enlarged explanatory view of a portion circumscribed by white line indicated in FIG. 1.

The filler of the present invention comprises at least one metal oxide and at least one water-soluble metal salt, the metal oxide and the water-soluble metal salt each forming an independent phase, and one of greatest features of the present invention resides in that the water-soluble metal salt phase comprises a crystal of the water-soluble metal salt having an average particle size of from 0.001 to 0.3 $\mu$m. Since the filler has the above constitution, the filler of the present invention, for instance, has the following excellent characteristics.

(1) Ion Releasability

Since the filler of the present invention comprises a fine crystal of a water-soluble metal salt as an ion-releasing source, rapid ion release takes place when the filler, for instance, is contacted with water. Therefore, when the filler is, for instance, used for a dental composite material, early exhibition of clinical effects, including the prevention of the onset and recurrence of dental caries can be accomplished.

(2) Water Resistance and Acid Resistance

Since the crystal of the water-soluble metal salt contained in the filler of the present invention is fine, there is no substantial influence on the filler structure due to the disintegration of the water-soluble metal salt phase in connection with the ion release. Therefore, when the filler is, for instance, used for a dental composite material, excellent water resistance and acid resistance are exhibited such that there are no effects associated with ion release in aqueous acidic conditions such as an oral cavity. For instance, the detachment of the filler from the dental composite material, the formation of a gap between the filler and the resin portion, and the formation of voids in the filler, unlike conventional ion-releasing fillers do not take place.

(3) Mechanical Strength

In the present invention, a metal oxide used as a constituent of a conventional inorganic filler having no ion releasability is used as a metal oxide, and this metal oxide mainly functions as the backbone for the filler of the present invention (specifically, it can be said that the metal oxide constitutes a domain phase, and the water-soluble metal salt constitutes a dispersion phase). Accordingly, the filler of the present invention has mechanical strength (mainly compression resistance) of the same level as that of conventional inorganic fillers. In addition, the filler of the present invention is excellent in water resistance and acid resistance as described above despite its ion releasability. Therefore, the structural disintegration does not take place in the filler even when exposed to an environment such as an oral cavity for a long period of time, and thereby the filler exhibits excellent durability.

(4) Aesthetic Appreciation

Since the crystal of the water-soluble metal salt contained in the filler of the present invention is fine, the water-soluble metal salt does not substantially affect the refractive index of the filler per se. Therefore, the transparency of the filler can be improved by appropriately selecting a metal oxide. The reduction of the difference in refractive indices between the filler and the resin constituting the composite material is effective for the improvement in the transparency of a dental composite material. In the present invention, the transparency of the composite material can be improved by simply adjusting the relationship between the metal oxide used in the filler and the resin used in the dental composite material in the aspect of the refractive indices of the metal oxide and the resin. For instance, the refractive index of the filler can easily be adjusted by adjusting the content of the metal oxide used, or changing the kinds of the metal oxide. In addition, besides the refractive index, the particle size of the crystal of the water-soluble metal salt contained in the filler is greatly involved with the improvement of the transparency of the dental composite material. Specifically, when the particle size of the crystal in the inner portion of the filler is large, light scattering in the inner portion becomes large, so that the transparency of the dental composite material is lowered. Since the particle size of the crystal of the water-soluble metal salt contained in the filler of the present invention is very small, when the filler is used for a dental composite material, the dental composite material can exhibit more excellent transparency, as compared to the case of a known ion-releasable filler having a comparable refractive index. Furthermore, since the filler of the present invention has excellent water resistance and acid resistance as described above, the filler does not show a change in external appearance even when exposed to an environment such as an oral cavity. As described above, the filler of the present invention is also excellent in aesthetic appreciation.

According to the present invention, there is provided a filler having highly excellent properties, as compared to those of conventional fillers, especially conventional ion-releasable fillers. The above filler is very useful as a constituent of the dental composite material. In addition, there is obtained a dental composite material excellent in water resistance, acid resistance, ion releasability, and aesthetic appreciation, by using the above filler.

The filler of the present invention comprises at least one metal oxide and at least one water-soluble metal salt each forming an independent phase. The phrase "forming an independent phase" as referred to herein means not that the metal oxide and the water-soluble metal salt are dissolved to give a completely homogeneous phase, but that the metal oxide and the water-soluble metal salt form separate phases. For instance, it is preferable that the phase comprising a crystal of the water-soluble metal salt is substantially homogeneously distributed in the metal oxide phase. The states of these phases, as shown in a photograph of FIG. 1 or FIG. 3, can be confirmed by using a scanning electron microscope (for instance, magnification: 30000 times) according to the method described in Examples set forth below.

The average particle size of the crystal of the water-soluble metal salt forming the water-soluble metal salt phase is within the range of from 0.001 to 0.3 $\mu$m, from the viewpoint of exhibiting the desired effects of the present invention. In addition, the average particle size of the above-mentioned crystal is preferably from 0.001 to 0.25 $\mu$m, more preferably from 0.001 to 0.2 $\mu$m, from the viewpoints of having more excellent transparency, water resistance and acid resistance of the filler, and further ion-releasability and transparency of the dental composite material comprising the filler. Further, since a more excellent product can be obtained for water resistance and acid resistance, the number ratio of crystals having a particle size of 0.3 $\mu$m or more is preferably 20% or less, more preferably 10% or less, still more preferably 5% or less. Here, the number of crystals refers to the number of dispersed phases in the domain phase. The particle size and the average particle size of the crystal can be obtained by the method described in Examples set forth below.

The metal oxide usable in the present invention is not limited to specified ones, and the metal oxide may be those metal oxides used for conventional dental fillers. For instance, the metal oxide may be those which are chemically stable without undergoing changes in the crystal structure and the molecular structure in the air at 350° C. or less. The metal oxide includes, for instance, silicon dioxide, boron oxide, aluminum oxide, titanium oxide, zinc oxide, strontium oxide, yttrium oxide, zirconium oxide, barium oxide, lanthanum oxide, ytterbium oxide and the like. In the present invention, at least one compound selected from the group consisting of these concretely exemplified metal oxides are preferable. Among them, silicon dioxide is more preferable, from the viewpoints of ion-releasability, transparency and production costs of the filler.

In addition, metal oxides containing an element having a large atomic number, for instance, zinc oxide, strontium oxide, yttrium oxide, zirconium oxide, barium oxide, lanthanum oxide, ytterbium oxide, and the like are especially preferable, from the viewpoint of X-ray shielding ability (opacity). At least one compound selected from the group consisting of these concretely exemplified metal oxides are further preferable.

Also, as the combination of the metal oxides, combinations of silicon dioxide with at least one compound selected from the group consisting of boron oxide, aluminum oxide, titanium oxide, zinc oxide, strontium oxide, yttrium oxide, zirconium oxide, barium oxide, lanthanum oxide and ytterbium oxide is preferable. Combinations of silicon dioxide with at least one compound selected from the group consisting of zinc oxide, strontium oxide, yttrium oxide, zirconium oxide, barium oxide, lanthanum oxide and ytterbium oxide are more preferable.

The water-soluble metal salt used in the present invention is not limited to specified ones, so long as the water-soluble metal salt may be those which dissolve in water to release ions, including those slightly dissolvable in water despite its very low water solubility. For instance, as the water-soluble metal salt, those having solubility in neutral water at 25° C. of 0.1% by weight or more are preferably used. As the water-soluble metal salt, fluorine-containing water-soluble metal salts are preferably used, from the viewpoints of giving re-calcification of tooth surfaces and resistance to caries of teeth. Concretely, there can be used lithium fluoride, sodium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, dianmin silver fluoride, ammonium fluoride, sodium hydrogenfluoride, ammonium hydrogenfluoride, potassium hydrogenfluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorodistannate (II), potassium hexafluorozirconate and the like.

Among them, the metal fluorides of Group I and II of the Periodic Table, lithium fluoride, sodium fluoride, rubidium fluoride, cesium fluoride, beryllium fluoride, magnesium fluoride, calcium fluoride, strontium fluoride, barium fluoride, and the like are preferable, and especially sodium fluoride is preferable.

The water-soluble metal salts other than the above-mentioned fluorine compounds include substances releasing calcium ions or phosphate ions, which are used as the materials for hydroxyapatite, by the dissolution of the metal salts in water, substances releasing carbonate ions or magnesium ions which are thought to accelerate the crystallization of the hydroxyapatite, and the like.

As the water-soluble metal salt, at least one compound selected from the group consisting of alkali metal phosphates, alkaline earth metal phosphates, alkali metal carbonates, alkaline earth metal carbonates, alkali metal chlorides and alkaline earth metal chlorides is preferably used. Concrete examples of these water-soluble metal salts include water-soluble calcium salts such as calcium bis (dihydrogenphosphate), tetracalcium phosphate and calcium chloride; water-soluble phosphates such as sodium phosphate, sodium monohydrogenphosphate, sodium dihydrogenphosphate, potassium phosphate, potassium monohydrogenphosphate and potassium dihydrogenphosphate; and the like.

Specifically, in the present invention, as the water-soluble salt, there can be preferably used (i) a fluorine compound, and/or (ii) at least one compound selected from the group consisting of alkali metal phosphates, alkaline earth metal phosphates, alkali metal carbonates, alkaline earth metal carbonates, alkali metal chlorides and alkaline earth metal chlorides.

One of the surprising characteristics exhibited by the filler of the present invention and the dental composite material comprising the filler resides in that the amount of release of ions such as fluorine ions from the water-soluble metal salt can be obtained at a high level upon the contact of these filler and dental composite material with water, and at the same time that the filler and the dental composite material are excellent in water resistance and acid resistance. In order to have the above-mentioned filler or dental composite material exhibit the characteristics described above, it is preferable that the metal oxide and the water-soluble metal salt are added so that the content of the metal oxide in the filler is from 60 to 95% by mol, and that the content of the water-soluble metal salt in the filler is from 5 to 40% by mol. It is more preferable that these compounds are added so that the content of the metal oxide is from 70 to 90% by mol, and the content of the water-soluble metal salt is from 10 to 30% by mol.

In the filler of the present invention, other components may be added so long as the exhibition of the desired effects of the present invention would not be hindered.

One of the characteristics of the filler of the present invention resides in that the water-soluble metal salt phase is distributed in a size having an average particle size of 0.3 $\mu$m or less in the inner portion of the metal oxide. The filler can be prepared by mixing a metal oxide and/or a hydrolyzed product of a hydrolysable organometallic compound (for instance, the metal alkoxide compound mentioned below or the like), which is a substance which can be a source of the metal oxide, with an aqueous solution of a water-soluble metal salt, and drying the resulting mixture. Before drying the mixture, the solvent may be previously removed by a method such as filtration as desired. In addition, after drying, the residue may be pulverized as desired. Further, concurrently with drying, a heat treatment may be simultaneously carried out by, for instance, maintaining the mixture under normal pressure, preferably at 50° to 180° C., more preferably at 50° to 150° C., for the purpose of the effective removal of the solvent and acceleration of the dehydration condensation of the hydrolyzed product of the metal alkoxide. The process for preparing the filler of the present invention is encompassed in the present invention.

More concretely, the preparation process includes, for instance, the followings:

1) a process comprising dispersing fine metal oxide particles having an average particle size of 0.1 $\mu$m or less (for instance, a metal oxide sol) in an aqueous solution of a water-soluble metal salt, evaporating water from the mixture, heat-treating the resulting solid residue to fuse the metal oxide fine particles, and pulverizing the resulting bulk of metal oxide particles;

2) a process comprising homogeneously mixing at least one hydrolysable organometallic compound with a water-containing solvent, hydrolyzing the hydrolysable organometallic compound under acidic, neutral or alkaline conditions, mixing the resulting aqueous solution of the hydrolyzed product with an aqueous solution of a water-soluble metal salt, forming a metal oxide and at the same time forming the water-soluble metal salt phase in the inner portion of the metal oxide; and as a similar process to above, 3) a process comprising hydrolyzing a hydrolysable organometallic compound to give a metal oxide in the form of sol, homogeneously mixing this metal oxide sol with an aqueous solution of a water-soluble metal salt, evaporating the solvent from the mixture, and pulverizing the resulting solid residue as desired. These processes are preferably employed in the present invention.

Examples of the above-mentioned metal oxide sol include, for instance, silica sol (for instance, one manufactured by Nissan Chemical Industries, Ltd. under the trade name of "SNOWTEX"), alumina sol, zirconia sol and titania sol.

Examples of the hydrolysable organometallic compound include the following organosilicon compounds, and the like. In the case of the organosilicon compound, a compound represented by $Si(OR)_4$, wherein R is a linear or branched alkyl group having 1 to 8 carbon atoms, for instance, methyl group, ethyl group, propyl group, isopropyl group, butyl group and the like, is especially preferable. In addition, as to compounds other than the organosilicon compound, organometallic compounds containing an element in the Group II, III or IV of the Periodic Table, for instance, Ti, Zr, Ba, La, Mg, Ni, Ta, and the like are preferable, and compounds represented by $MII(OR)_2$, $MIII(OR)_3$, $MIV(OR)_4$, wherein MII is a metal belonging to Group II; MIII is a metal belonging to Group III; MIV is a metal belonging to Group IV; and R is a linear or branched alkyl group having 1 to 8 carbon atoms, for instance, methyl group, ethyl group, propyl group, isopropyl group, butyl group and the like, can be preferably used. In addition, as represented by $Zr[Al(OC_3H_7)_4]_2$, multi-metal-containing alkoxides containing two or more metal alkoxides can be used in some cases.

In the above-mentioned preparation processes 2) and 3), when the solution containing a hydrolyzed product of a metal oxide or a metal oxide sol is mixed with the aqueous solution of the water-soluble metal salt, a transparent to semitransparent water-containing gel may be formed as a mixture in some cases. A process of evaporating a water-containing solvent from the water-containing gel to dry the gel is especially preferable as a process for preparing the filler of the present invention. After the gel is dried, a desired filler is obtained by properly pulverizing the resulting bulk as desired.

In the process for preparing the filler of the present invention, since the drying rate during drying the above-mentioned mixture is involved with the particle size of the crystal of the metal salt (size of the phase) constituting the water-soluble metal salt phase dispersed in the inner portion of the metal oxide phase in the filler, it is required to adjust the drying rate of the mixture so that the crystal has the desired average particle size. In other words, the water-soluble metal salt is gradually precipitated in the inner portion of the mixture together with the evaporation of water in the mixture. As the rate of the evaporation is higher, the particle size of the crystal tends to become larger. Therefore, in order to make the particle size of the crystal small, it is desired that the drying rate is set as slow as possible. It is preferable that the drying is carried out under normal pressure at room temperature (20° C.) to 180° C. for several hours to several dozen days or so.

The solvent for dissolving and/or dispersing the metal oxide and the water-soluble metal salt may be any of those which are easily removable and do not affect harmfully in dental applications. Besides water used in the above-mentioned exemplified processes, a lower alcohol such as methanol, ethanol or propanol can be used alone or in admixture with water. The lower alcohols can be used in combination of plural kinds. The hydrolysis and the pulverization in the process for preparing the filler of the present invention can be carried out in accordance with known processes.

It is preferable that the filler of the present invention obtained above is used for dental applications such as constituents for the dental composite material. Therefore, according to the present invention, there is further provided a dental composite material comprising the filler.

The dental composite material comprises a filler (a) of the present invention, a polymerizable monomer (b) and a polymerization initiator (c), and its constitution is the same as a known dental composite material except that the filler (a) of the present invention is contained.

The content of the filler (a) in the dental composite material of the present invention is not limited to specified ones so long as the desired effects of the present invention are obtained. It is preferable that the content of the filler (a) is from 1 to 90% by weight, from the viewpoints of securing the amount of fluorine ions released and the water (acid) resistance of the composite material. In addition, the content of the filler (a) is more preferably from 1 to 50% by weight, still more preferably from 5 to 30% by weight.

The dental composite material may be prepared by mixing the filler (a) mentioned above, the polymerizable monomer (b) and the polymerization initiator (c).

It is desired that the dental composite material has a higher transparency. In order to obtain the high transparency, it is preferable that the refractive index of the visible light of the filler constituting the composite material coincides as much as possible with that of the cured product (resin) of the dispersion medium in which the filler is dispersed.

Usually, the metal oxide having X-ray opacity or glass prepared from these oxides as raw materials which is used as the filler in the dental composite material has a high photorefractive index. Therefore, in order to increase the transparency of the dental composite material, it is desired that the refractive index of the formulated filler is adjusted preferably to a range of from 1.4 to 1.7 depending upon the refractive index of the resin formulated in the composite material. The filler described above is obtained, for instance, by formulating a metal oxide and a water-soluble metal salt so that their contents are within the above-mentioned preferred ranges. Concretely, when silicon dioxide is used as the metal oxide, it is preferable that silicon dioxide (or a mixture of silicon dioxide with another metal oxide) is formulated within the range of from 60 to 95% by mol, and that a water-soluble metal salt, preferably sodium fluoride (or a mixture of the water-soluble metal salt with another water-soluble metal salt) is formulated within the range of from 5 to 40% by mol, and it is more preferable that silicon dioxide (or a mixture of silicon dioxide with another metal oxide) is formulated within the range of from 70 to 90% by mol, and that sodium fluoride (or a mixture of sodium fluoride with another water-soluble metal salt) is formulated within the range of from 10 to 30% by mol.

In addition, the particle size of the filler (a) usable in the dental composite material can be properly selected in accordance with the purpose of the dental composite material, and the average particle size of the filler (a) is preferably within the range of from 1 to 20 $\mu$m, more preferably within the range of from 1 to 5 $\mu$m. Among them, those in which all of the particles have a particle size within the range of 0.1 to 100 $\mu$m are preferable.

It is preferable to use a hydrophobic polymerizable monomer as the polymerizable monomer (b) because the water resistance of the composite material is reinforced, in a case where, for instance, the dental composite material of the present invention is used as a dental filling restorative material, a crown composite material or a denture base composite material. The hydrophobic polymerizable monomer includes, for instance, monofunctional (meth)acrylates such as (meth)acrylates (for instance, in a case of an alkyl ester, those having an alkyl group having 1 to 12 carbon atoms; in a case of an aromatic group-containing ester, those having 6 to 12 carbon atoms, in which case the number of carbon atoms of a substituent is also counted for those groups having a substituent such as a polyethylene glycol chain); di(meth)acrylates of alkanediols and other polyfunctional (meth)acrylates; urethane (meth)acrylates, which are reaction products of 2 mol of (meth)acrylate having hydroxyl group with 1 mol of diisocyanate. Concretely, monomers disclosed in Japanese Examined Publication No. Sho 55-33687 and Japanese Patent Laid-Open No. Sho 56-152408; and the like are preferable.

Concrete examples of the monofunctional (meth)acrylate include (meth)acrylates such as methyl (meth)acrylate, ethyl (meth)acrylate, n-butyl (meth)acrylate, isobutyl (meth)acrylate, 2-ethylhexyl (meth)acrylate, lauryl (meth)acrylate, tridecyl (meth)acrylate, stearyl (meth)acrylate, cyclohexyl (meth)acrylate, benzyl (meth)acrylate, glycidyl (meth)acrylate, allyl (meth)acrylate, phenoxydiethylene glycol (meth)acrylate, phenoxyhexaethylene glycol (meth)acrylate, dicyclopentenyl (meth)acrylate, isobornyl (meth)acrylate, phenyl (meth)acrylate, caprolactone-modified tetrahydrofurfuryl (meth)acrylate, caprolactone-modified dipentaerythritol (meth)acrylate and caprolactone-modified 2-hydroxyethyl (meth)acrylate.

The bifunctional hydrophobic polymerizable monomer includes, for instance, 1,3-butylene glycol di(meth)acrylate, 1,6-hexanediol di(meth)acrylate, neopentyl glycol di(meth)acrylate, bisphenol A di(meth)acrylate, bisphenol A glycidyl di(meth)acrylate, ethylene oxide-modified bisphenol A di(meth)acrylate, ethylene oxide-modified bisphenol A glycidyl di(meth)acrylate, 2,2-bis(4-methacryloxypropoxyphenyl)propane, 7,7,9-trimethyl-4,13-dioxa-3,14-dioxo-5,12-diazahexadecane-1,1,6-diol di(meth)acrylate, neopentyl glycol hydroxypivalate di(meth)acrylate, caprolactone-modified neopentyl glycol hydroxypivalate di(meth)acrylate, trimethylolethane di(meth)acrylate, trimethylolpropane di(meth)acrylate, and the like.

The trifunctional or higher polyfunctional hydrophobic polymerizable monomer includes, for instance, trimethylolmethane tri(meth)acrylate, trimethylolethane tri(meth)acrylate, trimethylolpropane tri(meth)acrylate, pentaerythritol tri(meth)acrylate, dipentaerythritol tri(meth)acrylate, pentaerythritol tetra(meth)acrylate, dipentaerythritol tetra(meth)acrylate, dipentaerythritol hexa(meth)acrylate, and the like.

Besides them, there can be further exemplified ethylene oxide-modified (meth)acrylate in which (meth)acrylate is modified with ethylene oxide, a reaction product of 3-chloro-2-hydroxypropyl (meth)acrylate with methylcyclohexane diisocyanate, a reaction product of 2-hydroxypropyl (meth)acrylate with methylcyclohexane diisocyanate, a reaction product of 2-hydroxypropyl (meth)acrylate with methylenebis(4-methylcyclohexyl isocyanate), a reaction product of 2-hydroxypropyl (meth)acrylate with trimethylhexamethylene diisocyanate, a reaction product of 2-hydroxyethyl (meth)acrylate with isophorone diisocyanate, a reaction product of 3-chloro-2-hydroxypropyl (meth)acrylate with isophorone diisocyanate, and the like.

In addition, when the dental composite material of the present invention is used as a dental bonding agent or a dental cement, it is preferable to add a hydrophilic polymerizable monomer having a low molecular weight or a high molecular weight to the above-mentioned hydrophobic polymerizable monomer, in order to improve the adhesion of the composite material to teeth. The hydrophilic polymerizable monomer having a low molecular weight described above includes, for instance, 2-hydroxyethyl (meth)acrylate, 2-hydroxypropyl (meth)acrylate, 1,3- and 2,3-dihydroxypropyl (meth)acrylates, 2-hydroxypropyl-1,3-di (meth)acrylate, mono-, di- and tri(meth)acrylates of pentaerythritol, mono-, di- and tri(meth)acrylates of mesoerythritol, mono-, di- and tri(meth)acrylates of xylitol, (meth)acrylic acid, dimethylaminoethyl (meth)acrylate, hydrochloride of 2-trimethylammonium ethyl (meth) acrylate, 2-(meth)acrylamide-2-methylpropanesulfonic acid, (meth)acrylamide, 2-hydroxyethyl (meth)acrylamide, N,N-bis-(2-hydroxyethyl) (meth)acrylamide, an N-alkyl-N-hydroxyethyl (meth)acrylamide, 2- and 3-hydroxypropyl (meth)acrylamides, methacrylamide propyltrimethylammonium chloride, ethylene glycol di(meth)acrylate, mono- and di(meth)acrylates of diethylene glycol, mono- and di(meth) acrylates of triethylene glycol, tripropylene glycol di(meth) acrylate, 2-ethoxyethyl (meth)acrylate, methoxydiethylene glycol (meth)acrylate, methoxytetraethylene glycol (meth) acrylate, tetrahydrofurfuryl methacrylate, (meth)acrylate of pyrrolidone, (meth)acrylate of sorbitol, and the like.

Among the hydrophilic polymerizable monomers having a low molecular weight, the polymerizable monomer having in its molecule one or more acidic groups, for instance, phosphate group, pyrophosphate group, carboxylate group, sulfonate group or the like, is suitably used for improving the adhesion strength of the materials for root canal filling to teeth. Among the polymerizable monomers, the polymerizable monomer having phosphate group includes, for instance, 2-(meth)acryloyloxyethyl dihydrogenphosphate, 4-(meth)acryloyloxybutyl dihydrogenphosphate, 6-(meth) acryloyloxyhexyl dihydrogenphosphate, 8-(meth) acryloyloxyoctyl dihydrogenphosphate, 10-(meth) acryloyloxydecyl dihydrogenphosphate, 12-(meth) acryloyloxydodecyl dihydrogenphosphate, 20-(meth) acryloyloxyeicosyl dihydrogenphosphate, 1,3-di(meth) acryloyloxypropyl-2-dihydrogenphosphate, 2-(meth) acryloyloxyethyl phenyl hydrogenphosphate, 2-(meth) acryloyloxyethyl-2'-bromoethyl hydrogenphosphate, (meth) acryloyloxyethyl phenyl phosphate, and the like, and acid chlorides thereof.

As the hydrophilic polymerizable monomer having pyrophosphate group, there can be exemplified, for instance, di(2-(meth)acryloyloxyethyl) pyrophosphate and the like, and acid chlorides thereof. As the hydrophilic polymerizable monomer having the carboxylate group, there can be exemplified maleic acid, maleic anhydride, 4-(meth) acryloyloxyethoxycarbonyl phthalic acid, 4-(meth) acryloyloxyethoxycarbonyl phthalic acid anhydride, 5-(meth)acryloylaminopentylcarboxylic acid, N-(meth) acryloyl-5-aminosalicylic acid, 11-(meth)acryloyloxy-1,1-undecanedicarboxylic acid, and the like, and acid chlorides thereof. The hydrophilic polymerizable monomer having sulfonate group includes, for instance, 2-(meth)acrylamide-2-methylpropanesulfonic acid, styrenesulfonic acid, 2-sulfoethyl (meth)acrylate, and the like.

The hydrophilic polymerizable monomer having a high molecular weight, which is a so-called a macromer, includes, for instance, polyethylene glycol mono- and di(meth)acrylates, methoxypolyethylene glycol (meth) acrylate, polypropylene glycol mono- and di(meth)acrylates, methoxypolypropylene glycol (meth)acrylates, (meth) acrylates of polyvinyl alcohols, and the like.

The above-mentioned polymerizable monomers can be used alone or in admixture of two or more kinds.

The content of the polymerizable monomer (b) in the dental composite material of the present invention is not limited to specified ones. The content of the polymerizable monomer (b) is preferably from 5 to 99% by weight, more preferably from 10 to 90% by weight, from the viewpoint of exhibiting the desired effects of the present invention. In addition, as mentioned above, when polymerizable monomers having different characteristics are used, as in the case where, for instance, the improvement in the adhesion of the composite material to teeth is desired, the ratio of the contents of each monomer may be properly adjusted depending upon the desired effects.

The dental composite material of the present invention is provided in single packaging form, or two or more packaging forms. The composite material can be prepared by arbitrarily mixing the above-mentioned filler (a), the above-mentioned polymerizable monomer (b) and the polymerization initiator (c) by a known process for each packaging depending upon each form. The raw material composition of the contents of each packaging is not limited to specified ones, and those in which the dental composite material is not polymerized and cured during storage are preferable.

In the case where the dental composite material is provided in a single packaging form, it is preferable to use a photopolymerization initiator utilizing visible light as the polymerization initiator (c). As the photopolymerization initiator, there are preferably used, for instance, camphorquinone and amines described in Japanese Patent Laid-Open No. Sho 48-49875; camphorquinone, organic peroxides and amines described in Japanese Patent Laid-Open No. Sho 57-203007; camphorquinone and alkyl N,N-dimethylbenzoates described in Japanese Patent Laid-Open No. Sho 60-26002; camphorquinone, aldehydes and organic peroxides described in Japanese Patent Laid-Open No. Sho 60-149603; camphorquinone and mercaptan described in Japanese Patent Laid-Open No. Sho 60-197609; camphorquinone and azo compounds described in Japanese Patent Application No. Sho 61-290780; and the like.

Further, an acylphosphine oxide-based photopolymerization initiator can be also suitably used. The acylphosphine oxide includes, for instance, 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl di-(2, 6-dimethylphenyl) phosphonate, 2,4,6-trimethylbenzoylethoxyphenylphosphine oxide, water-soluble acylphosphine oxides disclosed in Japanese Examined Patent Publication No. Hei 3-57916, and the like.

The above-mentioned photopolymerization initiators can be used alone or in admixture of two or more kinds. In addition, the photopolymerization initiator may be used together with a reducing agent such as various amines, aldehydes, mercaptans and sulfonates.

When the dental composite material of the present invention is provided in a single packaging form, it is convenient and preferable that the dental composite material is polymerized and cured upon use by irradiating visible light with a visible light irradiator for dental use generally used in dental clinics.

Also, in the case of a single packaging form, a heat polymerization-type polymerization initiator can be used as the polymerization initiator (c). In this case, it is preferable to use a known polymerization initiator such as a peroxide or an azo compound, having an operable temperature range of from 40° to 100° C. Upon use, the dental composite material is polymerized and cured by properly heating by a known method depending upon the characteristic of the polymerization initiator used.

On the other hand, when the dental composite material of the present invention is provided in the form of two or more packagings, it is preferable that the contents of each package are formulated so that the polymerization and curing can be started by mixing the contents of each packing upon use. In this case, a redox radical polymerization initiator can be suitably used. The polymerization initiator as mentioned above comprises an oxidizing agent and a reducing agent, so that it is preferable that the oxidizing agent and the reducing agent are separately contained in divided packages to prevent the dental composite material from being polymerized during storage of the composite material.

The oxidizing agent includes, for instance, organic peroxides such as dialkyl peroxides, peroxy esters, diacyl peroxides, peroxy ketals, ketone peroxides and hydroperoxides. Among them, the diacyl peroxides are preferred. Concrete examples include benzoyl peroxide, 2,4-dichlorobenzoyl peroxide, m-toluoyl peroxide, and the like.

As the reducing agent, there can be suitably used aromatic tertiary amines such as diethanolp-toluidine, and aromatic sulfinic acids and aromatic sulfinates, such as benzenesulfinic acid, sodium benzenesulfinate and sodium 2,4,6-trimethylbenzenesulfinate.

These polymerization initiators listed above are used alone or in a combination of several kinds.

Usually, the content of the polymerization initiator in the composition of the dental composite material of the present invention is preferably within the range of from 0.01 to 20% by weight, more preferably within the range of from 0.1 to 5% by weight, irrespective to the kinds of the polymerization initiator.

In the dental composite material of the present invention, besides the raw materials mentioned above, there may be formulated known fillers and other additives. As the filler, there can be preferably used a known substance such as silicon dioxide particles such as silica, silica glass, fumed silica and synthesized silica prepared by sol-gel method; various glass materials such as those comprising silicon dioxide or alumina as a main component and further comprising boron or aluminum together with various heavy metals such as lanthanum, barium and strontium; various ceramics; diatomaceous earth, kaolin, clay minerals (montmorillonite and the like), activated clay, synthesized zeolite, mica, calcium fluoride, calcium phosphate, barium sulfate, zirconium dioxide and titanium dioxide. These fillers can be usually used alone or in combination of several kinds, and the formulation amount of the filler in the composite material is preferably within the range of from 5 to 90% by weight.

In addition, these fillers may be subjected to a surface treatment with a silane coupling agent, a surfactant or the like in accordance with the purposes. The surface treatment agent includes known coupling agents, for instance, organosilicon compounds, such as ω-methacryloxyalkyl trimethoxysilanes (for instance, those having the number of carbon atoms between methacryloxy group and silicon atom of from 3 to 12), ω-methacryloxyalkyl triethoxysilanes (for instance, those having the number of carbon atoms between methacryloxy group and silicon atom of from 3 to 12), vinyltrimethoxysilane, vinyltriethoxysilane, vinyltriacetoxysilane and aminopropyltriethoxysilane; polymerizable monomers having an acidic group, such as (meth) acryloyloxyalkyl hydrogenphosphates [for instance, those having the number of carbon atoms between (meth)acryloyl group and phosphate group of from 2 to 16], 2-(meth) acryloyloxyethyl phenyl phosphate, and 4-(meth) acryloyloxyethoxycarbonyl phthalate; and the like. As the surfactant, there can be used anionic surfactants such as metal salts of higher fatty acids, metal salts of alkyl phosphates and metal salts of alkylbenzenesulfonates; nonionic surfactants such as polyoxyethylene stearyl ether and sorbitan monolaurate; and the like.

The following components may be added to the composite material of the present invention, from the viewpoint of practical use and from the viewpoint of improvements in functionality. As the component which may be added from the viewpoint of practical use, there may be added as a polymerization inhibitor for suppressing the polymerization during storage, for instance, butylhydroxytoluene, dibutylhydroxytoluene, hydroquinone, hydroquinone monomethyl ether, or the like. Further, an antioxidant, a pigment, a dye or the like may be also added as desired. As the component which may be added from the viewpoint of improvements in functionality, there may be formulated for the purpose of imparting antibacterial property to the composite material, for instance, a polymerizable monomer having a cationic group such as (meth) acryloyloxyhexadecylpyridinium bromide, (meth) acryloyloxyhexadecylpyridinium chloride or (meth) acryloyloxydecylammonium chloride; a polymer having a cationic group such as polyhexamethylene diguanide hydrochloride; and the like.

The dental composite material of the present invention is used as, for instance, composite resins for dental fillers, composite resins for core build-up, crown composite resins, denture base resins, dental adhesive resin cements, dental fissure sealants, dental varnishes or coating agents, dental bonding agent, tooth adhesion primers, dental manicures, materials for root canal filling, and the like.

The dental composite material of the present invention has the property such that ions are released into water upon the contact of its polymerized and cured product with water. The releasing phenomenon of the ions into water can be quantitatively confirmed by immersing the polymerized and cured product of the composite material in ion-exchanged water or a buffer having a pH adjusted to near neutrality, determining the water-soluble metal salts eluted from the cured product and/or ions constituting the water-soluble metal salts by atomic absorption spectrophotometry or electrochemically with an ion electrode appropriate for the kinds of ions. As the amount released, it is preferable that the amount released in one day from the polished surface of 1 $cm^2$ of the polymerized and cured product of the composite material is at least 5 $\mu g$.

Various properties and characteristics of the filler and the dental composite material of the present invention can be evaluated by the methods described in Examples set forth below.

The present invention will be described in further detail by means of Examples, without intending to limit the scope of the present invention thereto. The test methods, the materials and the like used in Examples are summarized below.

(1) Preparation of Filler

Process A: An aqueous solution containing a saturated concentration of a water-soluble metal salt was prepared in a beaker equipped with a stirring motor. Thereafter, with vigorously stirring the aqueous solution of the water-soluble metal salt, a metal oxide sol was added dropwise thereto over a period of 10 minutes, so that the metal oxide and the water-soluble metal salt were in molar ratios as shown in Tables 1 and 2, to give a mixture of the metal oxide and the water-soluble metal salt. The rate of the dropwise addition may be properly adjusted in accordance with the reaction rate of the metal oxide with the water-soluble metal salt.

When the water-soluble metal salt is sodium fluoride, the sodium fluoride acted as a catalyst to form a network due to the condensation between colloidal particles, so that the above-mentioned mixture was gradually thickened and formed a hydrogel.

After the completion of the dropwise addition, the mixture was allowed to stand at room temperature overnight.

The mixture was transferred to a metallic vat, spread thinly over the vat into a thickness of 2 to 3 cm or so, and dried for 24 hours in a hot blow drier of 70° C. The drying was stopped at a point when there was no change in its weight, and the mixture was finely pulverized over a period of 15 hours with a rotary ball-mill.

Process B: A saturated aqueous solution of a water-soluble metal salt containing 0.1% ammonia was prepared. Thereafter, each metal alkoxide compound was uniformly dissolved in isopropyl alcohol containing 0.35 N hydrochloric acid, and this solution was stirred at room temperature for 2 hours to hydrolyze the metal alkoxide compound. With stirring the above-mentioned saturated aqueous solution, the solution of the metal alkoxide hydrolyzate was gradually added dropwise over a period of about 1 hour, so that the metal oxide and the water-soluble metal salt were in molar ratios as shown in Tables 1 and 2, to give a mixture of the metal oxide and the water-soluble metal salt. After the completion of the dropwise addition, the mixture was allowed to stand at room temperature overnight. The resulting mixture was dried in a hot blow drier of 50° C. until there was no change in its amount, and the dried product was roughly disintegrated, and then pulverized with a rotary ball-mill for a period of 15 hours, to give a filler.

Process C: The same procedures as in the process A were carried out, except that the mixture was dried in a hot blow drier of 200° C. until there was no change in its amount in the drying step.

(2) Preparation of Polymerizable Base Materials for Dental Composite Materials

Four kinds of polymerizable base materials (A to D) listed in Table 4 were prepared. A polymerizable monomer and a polymerization inhibitor dibutylhydroxytoluene were mixed in a specified composition to uniformly dissolve each of the components. Thereafter, a photopolymerization initiator or a redox polymerization initiator was added thereto, and the mixture was further stirred to uniformly dissolve the components.

(3) Preparation of Dental Composite Materials

A pulverized filler was kneaded together with other components in the compositions shown in Tables 1 and 2 with a glass mortar, to give a uniform paste. The resulting paste was defoamed under reduced pressure, and subjected to various evaluations.

(4) Preparation of Polymerized and Cured Products of Dental Composite Materials

The polymerized and cured product of the dental composite material used in the following test method was obtained by filling a dental composite material in the form of paste before polymerization in a stainless steel die with a disk-shaped opening having a given size, of which one side of the opening face was covered with a glass plate, thereafter pressing a glass plate onto the other side of the opening face of the die, and photoirradiating for 40 seconds from the both openings of the die through the glass plates with a visible light irradiator for dental use Lightel II (manufactured by Morita Seisakusho) to cause polymerization and curing.

(5) Electron Microscopic Observation

Using a scanning electron microscope S-4000 (manufactured by Hitachi Ltd.), the fine phase dispersion states in the filler of the various constituents contained in the filler of the present invention were observed, and the acid resistance for the polished surface described below was evaluated on the basis of secondary electron images.

The polymerized and cured product of the dental composite material comprising the filler was mirror-polished using a diamond paste, and the polished surface was washed with hexane so that the water-soluble substances contained in the filler and other fillers would not be eluted therefrom. In the fine structure observation of the filler of the present invention, the polished surface of the sample was vapor-deposited with carbon and the voltage applied to the electron gun was 5 keV. In the observation of the dispersion state of the metal oxide and the water-soluble metal salt, the difference in detection intensities of the secondary electron was utilized such that the conditions of vacuum vapor deposition of the electroconductive substance onto the sample surface and the voltage applied to the electron gun were adjusted so that the difference in the detection intensities of the secondary electron is optimized. In addition, the average particle size (nm) of the phase comprising crystal of the water-soluble metal salt in the filler was obtained by determining particle sizes for 100 particles optionally selected on an electron photomicrograph (the average of the longest length and the shortest length of the phase being taken as a particle size), and calculating its average. Furthermore, of the 100 determined particle sizes, a number ratio of particles having a particle size of 0.3 µm or more was calculated. Separately, in the electron microscopic observation in the acid resistance test for a polished surface described below, the sample surface was vacuum vapor-deposited with gold and palladium, and the voltage applied to the electron gun was 15 keV.

(6) X-ray Diffraction Test

The X-ray wide-angle diffraction was determined for various ion-releasable fillers obtained by the methods described above with a rotary anticathode X-ray diffractometer RINT-2400 (manufactured by Rigaku Corporation). Measurements were taken over the range of $2\theta=5°$ to $80°$ under the conditions of an applied voltage of 40 kV, an electric current of 100 mA, a target Cu, an X-ray wavelength (CuKα1) of $\lambda=1.5405$ Å, and a detector scanning speed of 1°/min.

(7) Transparency Test

The optical transparency of the filler itself of the present invention was evaluated by observation of light transmittance using a metal microscope OPTIPHOT (manufactured by Nikon Corporation). Specifically, the filler used in this test (0.1 g) was dispersed in a small amount of glycerol, and this slurry was placed on a slide glass and clamped with a cover glass to observe the slurry. The case where the inner portion of the particle is substantially optically uniformly transparent is evaluated as "excellent," and otherwise evaluated as "poor."

(8) Refractive Index Test

The filler of the present invention was dispersed in a given amount (0.1 g/mL) in an organic solvent of a known refractive index (prepared by mixing two or more organic solvents to adjust to various refractive index levels), the refractive index ($nD^{25}$) of the organic solvent that gave the maximum light transmittance for the dispersion at 589 nm was determined, and this refractive index was taken as the refractive index of the filler. The refractive index of the organic solvent was determined in the presence of an Na-D light source with an Abbe refractometer 1T (manufactured by Atago Co., Ltd.), and the light transmittance of the dispersion is determined in a quartz cell with an optical path length of 10 mm with an ultraviolet-visible light spectrophotometer UV-2400 (manufactured by Shimadzu Corporation).

(9) Ion Releasability Test

A cured product disk of a dental composite material of 1 mm in thickness and 18 mm in diameter was prepared, its surface was polished with SiC polishing paper #1000, and the disk was immersed in a phosphate buffer at pH 7, and stored for 1 month in a thermostatic chamber at 37° C. The amount of fluorine ions or calcium ions released into the phosphate buffer in a 1-month period was determined with a digital ion meter 920-A (manufactured by Orion) connected with a fluorine electrode or calcium electrode. The amount of ions released from the dental composite material was expressed as the amount of fluorine ions or calcium ions released per unit area ($\mu g/cm^2$) of the circular surface of the above-mentioned cured product disk.

(10) Acid Resistance Test for Polished Surface

A cured product disk of a dental composite material of 1 mm in thickness and 18 mm in diameter was prepared in the same manner as described above. Its surface was polished with SiC polishing paper #1500, and then with a diamond paste. The polished cured product disk was immersed in a citrate buffer at pH 5.6 for 7 days, and electron photomicrographs obtained before and after the immersion were compared. The acid resistance for the polished surface was evaluated as "excellent" in the case where there were substantially no generation of the detachment of the filler, the formation of a gap between the filler and the resin portion, the formation of a void in the filler, and the like, after the disk was immersed in the buffer at pH 5.6. Those with generation were evaluated as "poor."

In the present test, the acid resistance was evaluated using an acidic aqueous buffer. This experimental system is conducted under more severe conditions from the viewpoint of ion release as compared to a system in which the filler is simply contacted with water. Therefore, when the acid resistance was recognized in this experimental system, it can be said that the sample is also excellent in water resistance.

(11) Compressive Strength Test

Ten cylindrical cured products of a dental composite material of 4 mm in height and 4 mm in diameter were prepared, and immersed in water at 37° C. for 24 hours. For 5 of these cylindrical cured products, their compressive breaking strength was determined at a crosshead speed of 2 mm/min using a universal tester 1175 (manufactured by Instron Corporation) immediately after the immersion (initial compressive strength). The other 5 cured products were immersed in water at 4° C. and 60° C. alternately for 1 minute each in 10,000 cycles, and the compressive breaking strength was determined in the same manner as described above (compressive strength after 10,000 thermal cycles). In each case, the average of the five determinations was taken as the compressive strength (MPa) of the test material.

The test results obtained by the concrete examples are shown below. The specifications of the fillers used and the compositions of the dental composite materials comprising the fillers are shown in Tables 1 and 2. The specifications of the fillers other than the filler of the present invention formulated in the composite material are shown in Table 3. The compositions of the polymerizable base materials formulated in the composite material are shown in Table 4. The test results are shown in Tables 5 and 6.

EXAMPLES 1 and 2

Figure 3:
FIG. 3 is an electron microphotograph of an ion-releasable filler in Example 2.
Figure 4:
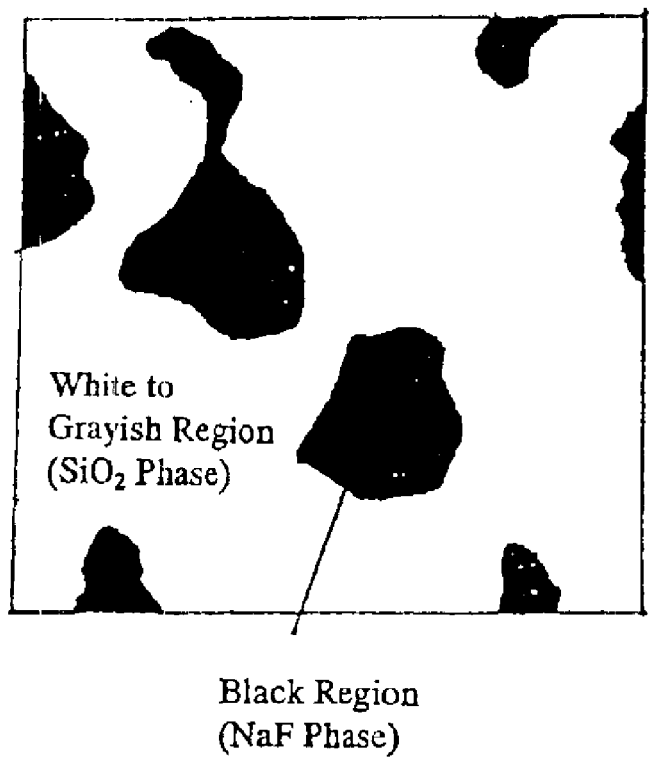
FIG. 4 is an enlarged explanatory view of a portion circumscribed by white line indicated in FIG. 3.
Figure 5:
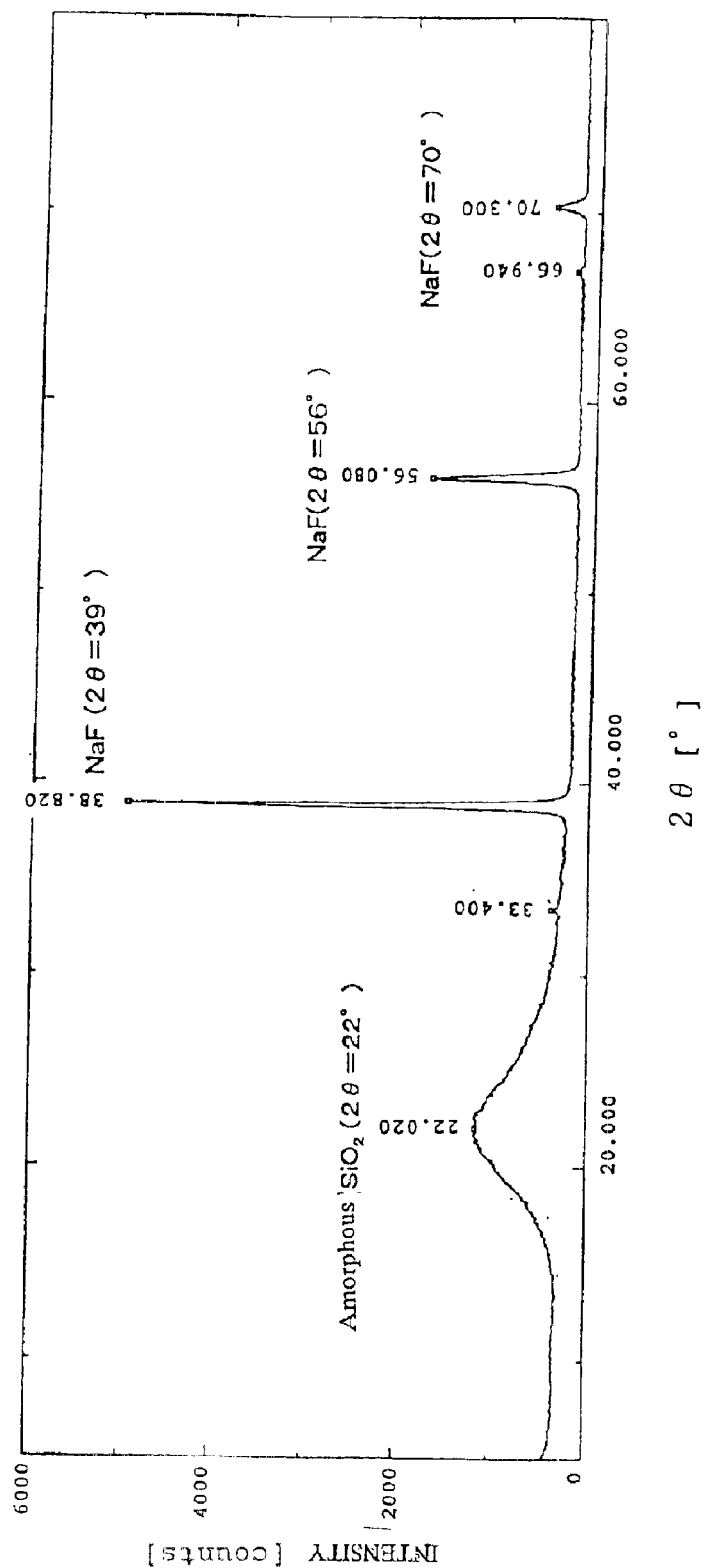
FIG. 5 is an X-ray diffraction chart of an ion-releasable filler in Example 1.
Figure 6:
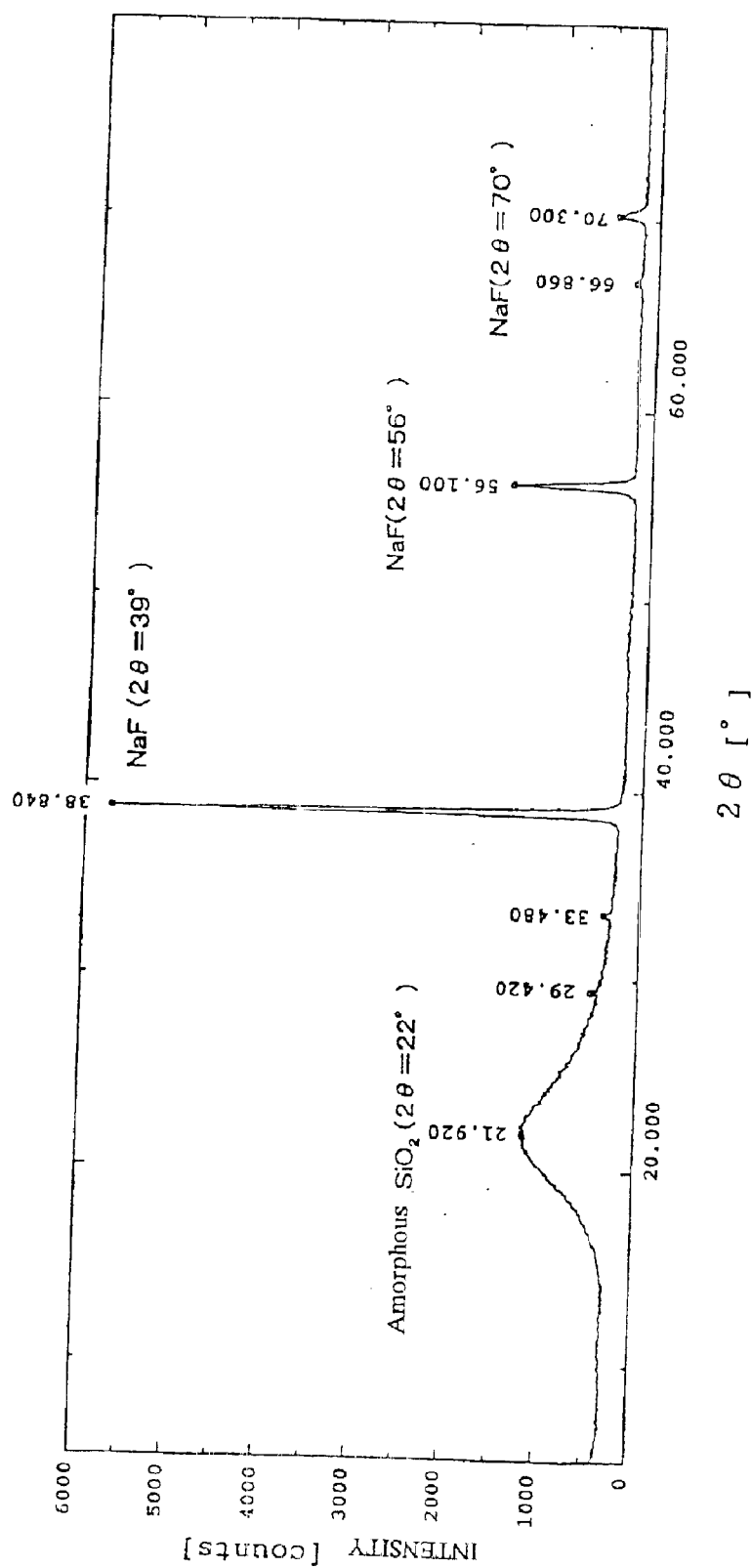
FIG. 6 is an X-ray diffraction chart of an ion-releasable filler in Example 2.

As metal oxides composing each of ion-releasable fillers, silica sols comprising colloidal particles having different shapes and particle sizes were used. A silica sol ST-50 (manufactured by Nissan Chemical Industries, Ltd.) used in Example 1 is a colloid having an average particle size of about 20 nm. A silica sol ST-PS-M (manufactured by Nissan Chemical Industries, Ltd.) used in Example 2 comprises particles having an average particle size of from 20 to 30 nm or so in the form of a branched string of beads having an overall particle size of from 100 to 200 nm. As a water-soluble metal salt, sodium fluoride was used. In both cases, a filler was prepared by the process A described in item (1) above. Both of the fillers obtained were excellent in optical transparency. The electron photomicrographs of cross-sectional views of each of the fillers are shown in FIGS. 1 and 3. It can be seen that both of the fillers form a homogenous matrix (phase) based on the binding of metal oxide colloidal particles, in which a fine dispersion phase of sodium fluoride is present independently.

An X-ray diffraction test of these fillers was conducted. As a result, in both Examples 1 and 2, it was confirmed that there were detected diffraction peaks (2θ=39°, 56°, 70°) ascribed to sodium fluoride crystals and a halo peak (2θ=22°) thought to be ascribed to amorphous $SiO_2$, and that ultrafine crystals of sodium fluoride were uniformly dispersed in the matrix comprising a silica colloid. It is thought that the optical transparency described above was achieved by the uniform dispersion of sodium fluoride on a nanometer scale. Dental composite materials using these fillers are excellent in the amount of fluorine ions released, excellent in acid resistance with no dissolution or detachment of the filler from the polished surface into water, and further excellent in the aesthetic appreciation and mechanical strength (compressive strength) durability.

EXAMPLE 3

There were used as metal oxides composing an ion-releasable filler, a silica sol ST-OL (manufactured by Nissan Chemical Industries, Ltd.) and a zirconia sol NZS-30A (manufactured by Nissan Chemical Industries, Ltd.), and as a water-soluble metal salt, sodium fluoride. An ion-releasable filler was prepared according to the process A described in item (1) above by uniformly mixing each of the aqueous solutions of the components so that silicon dioxide, zirconium oxide and sodium fluoride were in a molar ratio of 53:19:28. It can be seen that this filler shows a high refractive index of the same level as that of X-ray-shielding barium glass or the like widely used in dental composite materials, and is effective for improving the transparency of the dental composite materials. This filler was also excellent for other items, such as the amount of fluorine ions released.

EXAMPLES 4 to 7

An ion-releasable filler was prepared by the process B described in item (1) above using as raw materials for metal oxides composing each of ion-releasable fillers, a metal alkoxide compound such as tetraethyl orthosilicate (manufactured by Wako Pure Chemical Industries, Ltd.), zirconium tetra-n-butoxide (manufactured by Kanto Kagaku K.K.), aluminum isopropoxide (manufactured by Tokyo Kasei K.K.), or titanium isopropoxide (manufactured by Wako Pure Chemical Industries, Ltd.). In Examples 4 and 5, the refractive index of the filler was increased by the increase in the molar ratio of the zirconium oxide. The results show that the refractive index of the filler according to the present invention can be arbitrarily adjusted by the adjustment of the molar ratio of the metal oxides. On the other hand, it is shown in Examples 6 and 7 that the refractive index can be adjusted by the kinds of the metal oxides composing the filler (aluminum oxide, titanium oxide). In all of Examples 4 to 7, excellent results were obtained for other items, such as the amount of fluorine ions released.

EXAMPLE 8

A filler was prepared by the process A described in item (1) above, using as a metal oxide composing an ion-releasable filler, only Alumina Sol-200 (manufactured by Nissan Chemical Industries, Ltd.), a sol containing colloidal particles of aluminum oxide. The excellent results were obtained in the same manner as in Examples 1 and 2 in the cases where only the silica sols were used.

EXAMPLES 9 to 11

A filler was prepared by the process A described in item (1) above using as metal oxides composing each of ion-releasable fillers, a silica sol ST-PS-M (manufactured by Nissan Chemical Industries, Ltd.), the same one used as in Example 2, and as a water-soluble metal salt, sodium monofluorophosphate (manufactured by Aldrich) in Example 9, calcium primary phosphate (manufactured by Wako Pure Chemical Industries, Ltd.) in Example 10, and calcium chloride in Example 11. There were confirmed the release of fluorine ions from the dental composite material in Example 9 and the release of calcium ions from the dental composite material in Examples 10 and 11, whereby confirming that the filler is capable of releasing a component accelerating the calcination of the restored teeth. Excellent results were also obtained for other items.

EXAMPLES 12 and 13

An ion-releasable filler was prepared by the process A described in item (1) above using the same raw materials as in Example 1 with an increased or decreased amount of sodium fluoride as compared to that of Example 1. In Example 12, the amount of sodium fluoride in the filler was 5% by mol, fluorine ions being released in a sufficient amount for improving the acid resistance of teeth though the amount was small. Also, in Example 13 where the amount of sodium fluoride in the filler was large, a large amount of fluorine ions released was obtained. Further, in both cases, excellent results were obtained for other items.

EXAMPLES 14 and 15

The ion-releasable filler prepared in Example 2 was formulated in a dental composite material in an amount of 5% by weight in Example 14, and in an amount of 80% by weight in Example 15. In Example 15, the content of the ion-releasable filler was large, so that the amount of the fluorine ions released from the dental composite material was large. Nevertheless, the value of the compressive strength after the thermal cycles was not lowered, and showed excellent acidic resistance. Excellent results were also obtained for other items.

EXAMPLES 16 and 17

The ion-releasable filler prepared in Example 2 was mixed with a polymerizable base material comprising a hydrophilic monomer such as 2-hydroxyethyl methacrylate or a teeth adhesive monomer such as 10-methacryloyloxydecyl dihydrogenphosphate, and other fillers, to give a dental composite material. Even when a hydrophilic polymerizable monomer was used as a polymerizable base material, so that the amount of the ions released was dramatically increased, there was almost no decrease in the compressive strength after the thermal cycles. Excellent results were also obtained for other items.

COMPARATIVE EXAMPLE 1

An ion-releasable filler was prepared by the process C described in item (1) above using the raw materials having the same composition as in Example 1. The transparency of this filler was poor, and the acid resistance for the polished surface of the dental composite material comprising this filler was poor. The sample after the acid resistance test for the polished surface was subjected to an SEM observation. As a result, there were confirmed detachment or dissolution of the filler from the polished surface and formation of voids in the inner portion of the filler, showing that sodium fluoride crystals having particle sizes of the order of micrometer are present in the inner portion of the fluorine ion-releasable filler. By comparing with Examples 1 and 2, it is suggested that a structure in which sodium fluoride crystals having an average particle size of at most 300 nm are substantially uniformly dispersed in a silicon dioxide matrix is important for securing the transparency of the filler or the acid resistance of the polished surface of the dental composite material.

COMPARATIVE EXAMPLE 2

Each of the raw materials was mixed in accordance with the composition of Table 2, to give a dental composite material containing 5% by weight of sodium fluoride crystal powder (average particle size: 2.8 μm, particle size range: 0.1 to 25 μm) as an ion-releasable filler. While the amount of fluorine ions released from the dental composite material was excellent, the acid resistance for the polished surface was dramatically poor, and the compressive strength after the thermal cycles was also lowered.

COMPARATIVE EXAMPLE 3

A silica sol ST-50 (manufactured by Nissan Chemical Industries, Ltd.) was spread over a metallic vat so as to have a thickness of 2 to 3 cm, and dried until there was no weight change in a hot air dryer at 70° C. The resulting dried white solid was pulverized with a mortar to a particle size of about 1 mm, and thereafter pulverized with a rotary ball-mill for 24 hours. A dental composite material was prepared in accordance with the composition of Table 2 using the resulting powder. The properties of the dental composite material were evaluated. As a result, while the dental composite material was excellent in the acid resistance for the polished surface and the compressive strength after the thermal cycles, no fluorine ions were released therefrom.

COMPARATIVE EXAMPLE 4

Polysiloxane-coated sodium fluoride particles were prepared in reference to Japanese Patent Laid-Open No. Hei 10-36116. To a mixed solution of 100 g of vinyltriethoxysilane and 100 g of water was added 0.2 g of acetic acid, and the mixture was stirred at room temperature until the system became homogeneous. After saturated aqueous NaCl was added to this aqueous solution, the solution was extracted with ethyl acetate. An ethyl acetate solution was washed with an aqueous sodium hydrogencarbonate. After removing acetic acid, an ethyl acetate solution was dried over anhydrous sodium sulfate or anhydrous magnesium sulfate. The desiccant was removed by filtration, and ethyl acetate was distilled off under reduced pressure. As a result, 23 g of a hydrolyzed vinyltriethoxysilane was obtained. Ten grams of the hydrolyzed vinyltriethoxysilane was dissolved in 10 g of toluene, and 0.5 g of 3-aminopropyltriethoxysilane was further added thereto as a curing catalyst. The resulting solution was added to 10 g of sodium fluoride powder (average particle size: 2.8 μm, particle size range: 0.1 to 25 μm), and the mixture was stirred. Thereafter, toluene was distilled off under reduced pressure, and subsequently the residue was heat-treated at 120° C. for 30 minutes, to give 19 g of a white solid.

A dental composite material was prepared using the resulting powder as an ion-releasable filler. While the dental composite material had a large amount of fluorine ions released and was excellent in the compressive strength after the thermal cycles, the filler was poor in transparency and the dental composite material was poor in the acid resistance for the polished surface.

COMPARATIVE EXAMPLE 5

A dental composite material was prepared by using the fluoroaluminosilicate glass G018-117 having an average particle size of about 1.5 μm as an ion-releasable filler. While the dental composite material had a large amount of fluorine ions released, the dental composite material was poor in the acid resistance for the polished surface, and the lowering of the compressive strength after the thermal cycles was somewhat larger.

TABLE 1

| | Filler | | | |
|---|---|---|---|---|
| | Composition (mol %) | Water-Soluble Metal Salt | Metal Oxide | Process |
| Example 1 | $SiO_2$: 75<br>NaF: 25 | Sodium Fluoride | Silica Sol ST-50<br>(mfd. by Nissan Chemical) | A |
| Example 2 | $SiO_2$: 75<br>NaF: 25 | Sodium Fluoride | Silica Sol ST-PS-M<br>(mfd. by Nissan Chemical) | A |
| Example 3 | $SiO_2$: 53<br>$ZrO_2$: 19<br>NaF: 28 | Sodium Fluoride | Silica Sol ST-OL<br>(mfd. by Nissan Chemical)<br>Zirconia Sol NZS-30A<br>(mfd. by Nissan Chemical) | A |
| Example 4 | $SiO_2$: 53<br>$ZrO_2$: 19<br>NaF: 28 | Sodium Fluoride | Tetraethyl Orthosilicate<br>(mfd. by Wako Pure Chemical)<br>Zirconium Tetra-n-butoxide<br>(mfd. by Kanto Kagaku) | B |
| Example 5 | $SiO_2$: 44<br>$ZrO_2$: 28<br>NaF: 28 | Sodium Fluoride | Tetraethyl Orthosilicate<br>(mfd. by Wako Pure Chemical)<br>Zirconium Tetra-n-butoxide<br>(mfd. by Kanto Kagaku) | B |
| Example 6 | $SiO_2$: 61<br>$Al_2O_3$: 11<br>NaF: 28 | Sodium Fluoride | Tetraethyl Orthosilicate<br>(mfd. by Wako Pure Chemical)<br>Aluminum Isopropoxide<br>(mfd. by Tokyo Kasei) | B |
| Example 7 | $SiO_2$: 53<br>$TiO_2$: 19<br>NaF: 28 | Sodium Fluoride | Tetraethyl Orthosilicate<br>(mfd. by Wako Pure Chemical)<br>Titanium Isopropoxide<br>(mfd. by Wako Pure Chemical) | B |
| Example 8 | $Al_2O_3$: 75<br>NaF: 25 | Sodium Fluoride | Alumina Sol 200<br>(mfd. by Nissan Chemical) | A |
| Example 9 | $SiO_2$: 75<br>$Na_2PO_3F$: 25 | Sodium Monofluorophosphate | Silica Sol ST-PS-M<br>(mfd. by Nissan Chemical) | A |
| Example 10 | $SiO_2$: 90<br>$Ca(H_2PO_4)_2$: 10 | Calcium Primary Phosphate | Silica Sol ST-PS-M<br>(mfd. by Nissan Chemical) | A |
| Example 11 | $SiO_2$: 90<br>$CaCl_2$: 10 | Calcium Chloride | Silica Sol ST-PS-M<br>(mfd. by Nissan Chemical) | A |
| Example 12 | $SiO_2$: 95<br>NaF: 5 | Sodium Fluoride | Silica Sol ST-50<br>(mfd. by Nissan Chemical) | A |
| Example 13 | $SiO_2$: 60<br>NaF: 40 | Sodium Fluoride | Silica Sol ST-50<br>(mfd. by Nissan Chemical) | A |
| Example 14 | $SiO_2$: 75<br>NaF: 25 | Sodium Fluoride | Silica Sol ST-PS-M<br>(mfd. by Nissan Chemical) | A |
| Example 15 | $SiO_2$: 75<br>NaF: 25 | Sodium Fluoride | Silica Sol ST-PS-M<br>(mfd. by Nissan Chemical) | A |

| | Filler | | Dental Composite Material | | |
|---|---|---|---|---|---|
| | Average Particle Size (nm) of Water-Soluble Metal Salt Phase | Ratio (%) of Particles Having Particle Size of 0.3 · m or More | Filler (% by weight) | Other Fillers[1] (% by weight) | Polymerizable Base Material[2] (% by weight) |
| Example 1 | 142 | 0 | 10 | A: 72<br>B: 3 | A: 15 |
| Example 2 | 108 | 0 | 10 | A: 72<br>B: 3 | A: 15 |
| Example 3 | 152 | 0 | 10 | A: 72<br>B: 3 | A: 15 |
| Example 4 | 168 | 0 | 10 | A: 72<br>B: 3 | A: 15 |
| Example 5 | 189 | 2 | 10 | A: 72<br>B: 3 | A: 15 |

TABLE 1-continued

| | | | | | |
|---|---|---|---|---|---|
| Example 6 | 133 | 0 | 10 | A: 72<br>B: 3 | A: 15 |
| Example 7 | 195 | 1 | 10 | A: 72<br>B: 3 | A: 15 |
| Example 8 | 188 | 2 | 10 | A: 72<br>B: 3 | A: 15 |
| Example 9 | 95 | 0 | 10 | A: 72<br>B: 3 | A: 15 |
| Example 10 | 198 | 3 | 10 | A: 72<br>B: 3 | A: 15 |
| Example 11 | 193 | 1 | 10 | A: 72<br>B: 3 | A: 15 |
| Example 12 | 155 | 0 | 10 | A: 72<br>B: 3 | A: 15 |
| Example 13 | 153 | 0 | 10 | A: 72<br>B: 3 | A: 15 |
| Example 14 | 108 | 0 | 5 | A: 77<br>B: 3 | A: 15 |
| Example 15 | 108 | 0 | 80 | B: 5 | A: 15 |

[1]See Table 3,
[2]See Table 4

TABLE 2

| | | Filler | | | | |
|---|---|---|---|---|---|---|
| | Composition (mol %) | Water-Soluble Metal Salt | Metal Oxide | Process | Average Particle Size (nm) of Water-Soluble Metal Salt Phase | Ratio (%) of Particles Having Particle Size of 0.3 · m or More |
| Example 16 | $SiO_2$: 75<br>NaF: 25 | Sodium Fluoride | Silica Sol ST-PS-M (mfd. by Nissan Chemical) | A | 108 | 0 |
| Example 17 | $SiO_2$: 75<br>NaF: 25 | Sodium Fluoride | Silica Sol ST-PS-M (mfd. by Nissan Chemical) | A | 108 | 0 |
| Comparative Example 1 | $SiO_2$: 75<br>NaF: 25 | Sodium Fluoride | Silica Sol ST-50 (mfd. by Nissan Chemical) | C | 383 | 58 |
| Comparative Example 2 | NaF: 100 | Sodium Fluoride | — | — | 2800 | 94 |
| Comparative Example 3 | $SiO_2$: 100 | — | Silica Sol ST-50 (mfd. by Nissan Chemical) | — | — | — |
| Comparative Example 4 | | Polysiloxane-Coated Sodium Fluoride | | | 2800 | 94 |
| Comparative Example 5 | | Fluoroaluminosilicate Glass G018-117 (mfd. by Shott), product treated with silane | | | — | — |

| | Dental Composite Material | | |
|---|---|---|---|
| | Filler (% by weight) | Other Fillers[1] (% by weight) | Polymerizable Base Material[2] (% by weight) |
| Example 16 | 5 | C: 10 | B: 85 |
| Example 17 | 10 | B: 3<br>D: 60 | D: 27 |
| Comparative Example 1 | 10 | A: 72<br>B: 3 | A: 15 |
| Comparative Example 2 | 5 | A: 77<br>B: 3 | A: 15 |
| Comparative Example 3 | 10 | A: 72<br>B: 3 | A: 15 |
| Comparative Example 4 | 10 | A: 72<br>B: 3 | A: 15 |
| Comparative Example 5 | 85 | — | A: 15 |

[1]See Table 3,
[2]See Table 4

TABLE 3

| Filler | Kind | Specifications |
|---|---|---|
| A | Surface-treated, pulverized barium glass filler | 8235 (manufactured by Shott), average particle size: 2 μm, $nD^{25}$ = 1.55 |
| B | Surface-treated fumed silica filler | Aerozil 130 (manufactured by Nippon Aerozil Co., Ltd.) |
| C | Fumed silica filler | Aerozil R972 (manufactured by Nippon Aerozil Co., Ltd.) |
| D | Surface-treated, pulverized silica glass filler | G018-066 (manufactured by Shott), average particle size: 2 μm, $nD^{25}$ = 1.45 |

TABLE 4

| Polymerizable Base Material | Constituents | Parts by Weight |
|---|---|---|
| A | Bisphenol A Glycidyl Dimethacrylate | 68 |
| | Triethylene Glycol Dimethacrylate | 32 |
| | dl-Camphorquinone | 0.2 |
| | Ethyl Dimethylaminobenzoate | 0.1 |
| | 2,4,6-Trimethylbenzoyl Diphenylphosphine Oxide | 0.5 |
| | Dibutylhydroxytoluene | 0.02 |
| B | Bisphenol A Glycidyl Dimethacrylate | 40 |
| | 2-Hydroxyethyl Methacrylate | 35 |
| | Neopentyl Glycol Dimethacrylate | 20 |
| | 10-Methacryloyloxydecyl Dihydrogenphosphate | 5 |
| | dl-Camphorquinone | 1 |
| | Ethyl Dimethylaminobenzoate | 2 |
| | Dibutylhydroxytoluene | 0.02 |
| C | Bisphenol A Glycidyl Dimethacrylate | 40 |
| | Triethylene Glycol Dimethacrylate | 40 |
| | 10-Methacryloyloxydecyl Dihydrogenphosphate | 20 |
| | Benzoyl Peroxide | 2 |
| | Dibutylhydroxytoluene | 0.04 |
| D | Bisphenol A Glycidyl Dimethacrylate | 40 |
| | Triethylene Glycol Dimethacrylate | 30 |
| | 2-Hydroxyethyl Methacrylate | 30 |
| | Sodium 2,4,6-Triisopropylbenzenesulfinate | 1 |
| | N,N-Diethanol-p-toluidine | 2 |
| | Dibutylhydroxytoluene | 0.02 |

TABLE 5

| | Filler Transparency | Refractive Index ($nD^{25}$) | Amount of Ions Released (μg/cm²) | Acid Resistance | Compressive Strength (MPa) At Start | Compressive Strength (MPa) After 10000 Thermal Cycles |
|---|---|---|---|---|---|---|
| Example 1 | Excellent | 1.471 | 152 (F⁻) | Excellent | 468 | 461 |
| Example 2 | Excellent | 1.467 | 273 (F⁻) | Excellent | 475 | 467 |
| Example 3 | Excellent | 1.493 | 135 (F⁻) | Excellent | 462 | 457 |
| Example 4 | Excellent | 1.491 | 128 (F⁻) | Excellent | 471 | 465 |
| Example 5 | Excellent | 1.531 | 103 (F⁻) | Excellent | 455 | 462 |
| Example 6 | Excellent | 1.548 | 144 (F⁻) | Excellent | 475 | 453 |
| Example 7 | Excellent | 1.568 | 130 (F⁻) | Excellent | 461 | 458 |
| Example 8 | Excellent | 1.515 | 112 (F⁻) | Excellent | 475 | 462 |
| Example 9 | Excellent | 1.524 | 189 (F⁻) | Excellent | 475 | 459 |
| Example 10 | Excellent | 1.533 | 78 (Ca²⁺) | Excellent | 482 | 479 |
| Example 11 | Excellent | 1.523 | 43 (Ca²⁺) | Excellent | 491 | 461 |
| Example 12 | Excellent | 1.488 | 32 (F⁻) | Excellent | 478 | 468 |
| Example 13 | Excellent | 1.450 | 171 (F⁻) | Excellent | 471 | 455 |
| Example 14 | Excellent | 1.467 | 164 (F⁻) | Excellent | 462 | 460 |
| Example 15 | Excellent | 1.467 | 872 (F⁻) | Excellent | 419 | 395 |
| Example 16 | Excellent | 1.467 | 511 (F⁻) | Excellent | 305 | 285 |
| Example 17 | Excellent | 1.467 | 345 (F⁻) | Excellent | 335 | 321 |
| Comp. Example 1 | Poor | 1.466 | 128 (F⁻) | Poor | 455 | 375 |
| Comp. Example 2 | Excellent | 1.340 | 205 (F⁻) | Poor | 461 | 318 |
| Comp. Example 3 | Excellent | 1.455 | 0 | Excellent | 481 | 477 |
| Comp. Example 4 | Poor | 1.449 | 223 (F⁻) | Poor | 471 | 462 |
| Comp. Example 5 | Excellent | 1.515 | 214 (F⁻) | Poor | 465 | 412 |

Note: Amount of Ions Released units shown as (μg/cm²).

EXAMPLE 18

A small amount of hydrochloric acid was added to 18 g of water, and 52 g of tetraethyl orthosilicate (manufactured by Wako Pure Chemical Industries, Ltd.) was added thereto, and the mixture was stirred for about 1 hour until the mixture became uniform, to hydrolyze tetraethyl orthosilicate. Further, an aqueous sodium fluoride prepared by dissolving 2 g of sodium fluoride (manufactured by Wako Pure Chemical Industries, Ltd.) in 50 g of water was gradually added dropwise to the resulting aqueous hydrolysate solution. The mixed solution was transferred to a stainless vat and thinly spread over the vat, and dried in a hot air dryer of 70° C. for 24 hours, and thereafter pulverized with a rotary ball-mill over a period of 15 hours, to give 17 g of a white powder. The average particle size of the sodium fluoride phase was 0.152 μm, and the ratio of those particles having particle sizes of 0.3 μm or more was 0%.

A dental composite material was prepared by using the resulting white powder as an ion-releasable filler.

Specifically, a polymerizable base material A listed in Table 4 was used as a polymerizable monomer composition. Further, the filler A and the filler B listed in Table 3 were used. Here, the filler A is a surface-treated, pulverized barium glass filler prepared by surface-treating 100 parts by weight of a barium-containing glass powder (8235, manufactured by Shott) with 2 parts by weight of γ-methacryloxypropyl trimethoxysilane (hereinafter referred to as γ-MPS), the filler having an average particle size of 2 μm and a particle size range of from 0.1 to 15 μm. Also, the filler B is a powder prepared by surface-treating 100 parts by weight of a highly dispersible fumed silica powder (Aerozil 130 manufactured by Nippon Aerozil Co., Ltd.) with 40 parts by weight of the γ-MPS.

Figure 7:
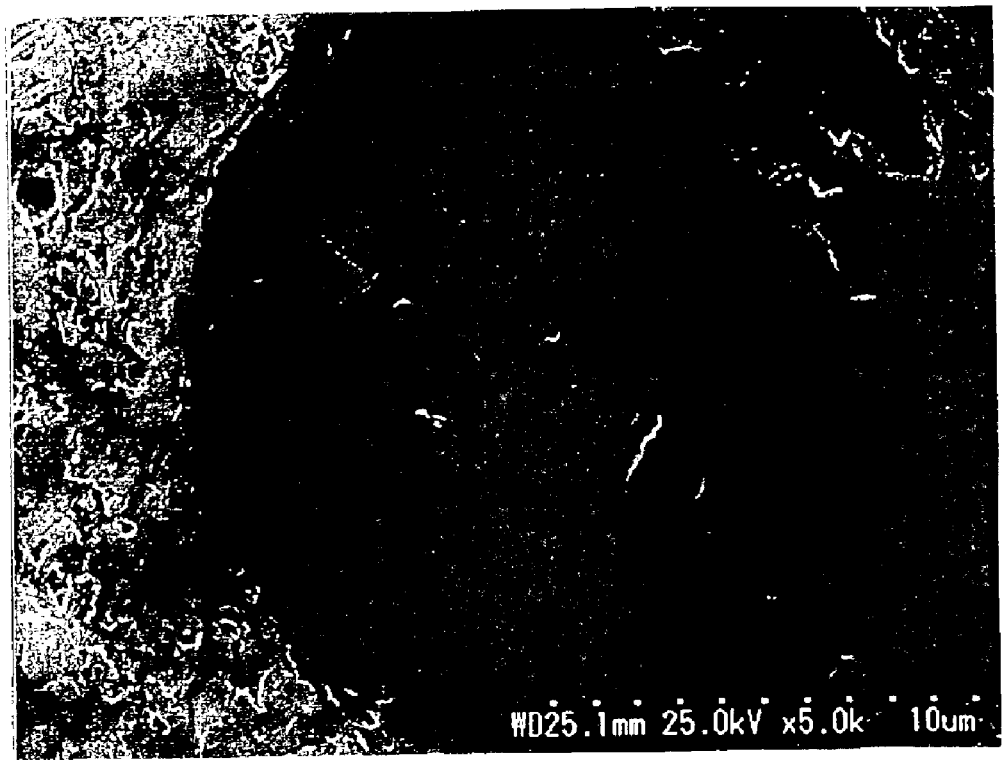
FIG. 7 is an electron microphotograph of a dental composite material surface after immersing the dental composite material in citrate buffer in an acid resistance test for a polished surface in Example 18.

A paste-like dental composite material was prepared by mixing respectively a polymerizable base material A 22% by weight, an ion-releasable filler 10% by weight, the filler A 65% by weight, and the filler B 3% by weight. Various tests mentioned above were conducted for the resulting filler and dental composite material. These test results are shown in Table 6. In addition, the electron microphotograph of the surface of the dental composite material after the acid resistance test is shown in FIG. 7.

COMPARATIVE EXAMPLE 6

A fine sodium fluoride powder was prepared with reference to Examples described in Japanese Patent Laid-Open No. Hei 2-258602. Concretely, an aqueous sodium fluoride prepared by dissolving 1 g of sodium fluoride in 100 g of water was solidified in a methanol bath at −60° C., and thereafter water was sublimed under reduced pressure, to give a fine sodium fluoride powder (average particle size: 0.44 μm, ratio of those particles having particle sizes of 0.3 μm or more: 38%, particle size range: 0.1 to 1.1 μm).

A liquid mixture prepared by dispersing 2 g of the fine sodium fluoride powder in 50 g of ethanol was gradually added to an aqueous hydrolysate solution of tetraethyl orthosilicate prepared in the same manner as in Example 18. Thereafter, in the subsequent procedures, drying and pulverization were carried out in the same manner as in Example 18, to give 18 g of a white powder.

Figure 8:
FIG. 8 is an electron microphotograph of a dental composite material surface after immersing the dental composite material in citrate buffer in an acid resistance test for a polished surface in Comparative Example 6.
Figure 9:
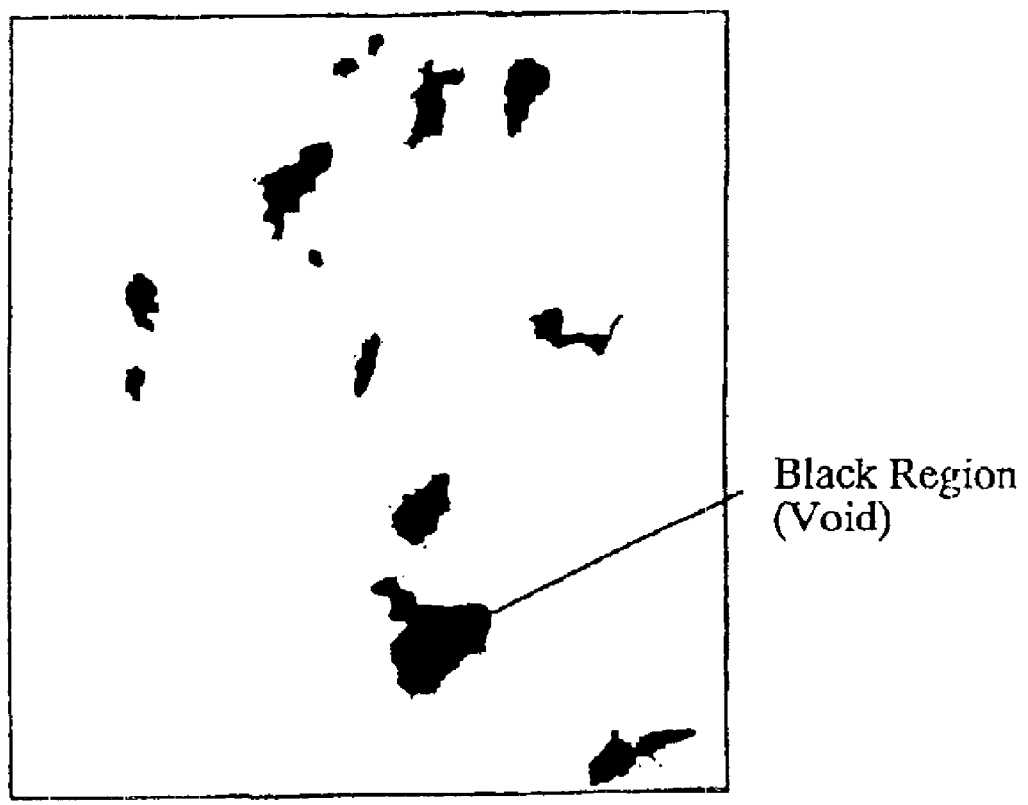
FIG. 9 is a schematic explanatory view of FIG. 8.

A dental composite material was prepared by using the resulting white powder as an ion-releasable filler, and using the same polymerizable base material A, filler A and filler B as those in Example 18 in the same composition. The same tests as those of Example 18 were conducted using the resulting filler and dental composite material. These test results are shown in Table 6. In addition, the electron microphotograph of the surface of the dental composite material after the acid resistance test is shown in FIG. 8.

EXAMPLE 19

An ion-releasable filler obtained in Example 2, namely an ion-releasable filler comprising a silica sol ST-PS-M (manufactured by Nissan Chemical Industries, Ltd.) and sodium fluoride was similarly prepared. Concretely, an aqueous sodium fluoride prepared by dissolving 2 g of sodium fluoride in 50 g of water was gradually added to 42.75 g of silica sol. Thereafter, in the subsequent procedures, drying and pulverization were carried out in the same manner as in Example 18, to give 17 g of a white powder (ion-releasable filler). The sodium fluoride phase had an average particle size of 0.088 μm and a ratio of those particles having particle sizes of 0.3 μm or more was 0%.

Figure 10:
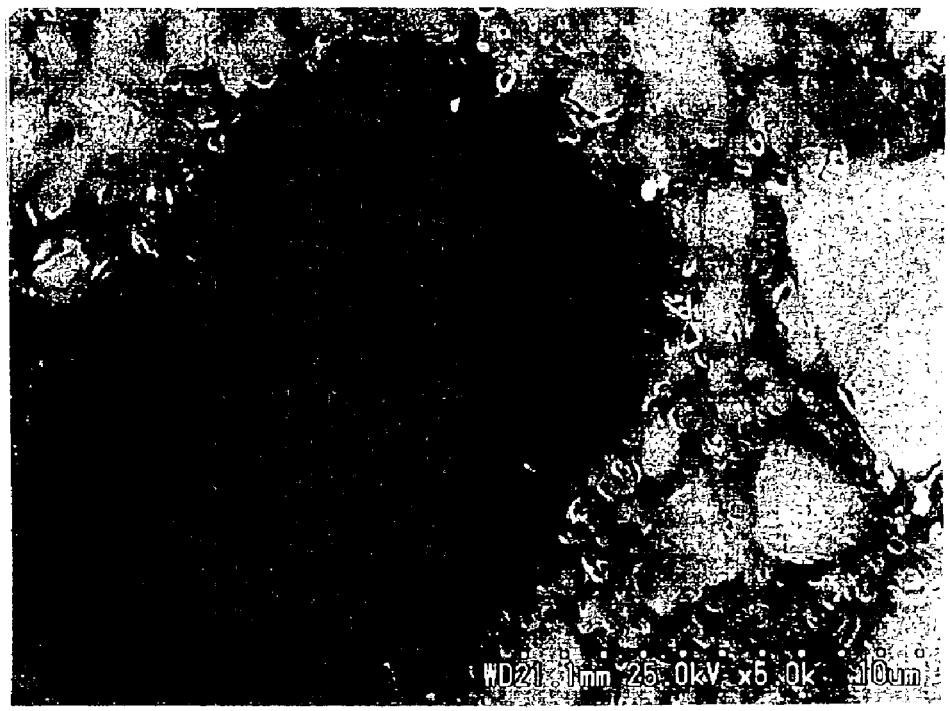
FIG. 10 is an electron microphotograph of a dental composite material surface after immersing the dental composite material in citrate buffer in an acid resistance test for a polished surface in Example 19.

A dental composite material was prepared by kneading the polymerizable base material A 15% by weight, the filler A 72% by weight, the filler B 3% by weight, which were the same components as those in Example 18, and the above-mentioned ion-releasable filler 10% by weight. The same tests as in Example 18 were conducted using the resulting filler and dental composite material. These test results are shown in Table 6. In addition, the electron microphotograph of the surface of the dental composite material after the acid resistance test is shown in FIG. 10.

COMPARATIVE EXAMPLE 7

An ion-releasable filler was prepared by using the silica sol used in Example 19 and the fine sodium fluoride powder obtained in Comparative Example 6. Specifically, the ion-releasable filler was prepared in the same manner as in Example 19 except that a dispersion prepared by dispersing the fine sodium fluoride powder obtained in Comparative Example 6 in ethanol was used in place of the aqueous sodium fluoride used in Example 19. Concretely, a sodium fluoride dispersion prepared by dispersing 2 g of a fine sodium fluoride powder in 50 g of ethanol was gradually added to 42.75 g of a silica sol, and in the subsequent procedures, drying and pulverization were carried out in the same manner as in Example 18, to give 17 g of a white powder.

Figure 11:
FIG. 11 is an electron microphotograph of a dental composite material surface after immersing the dental composite material in citrate buffer in an acid resistance test for a polished surface in Comparative Example 7.
Figure 12:
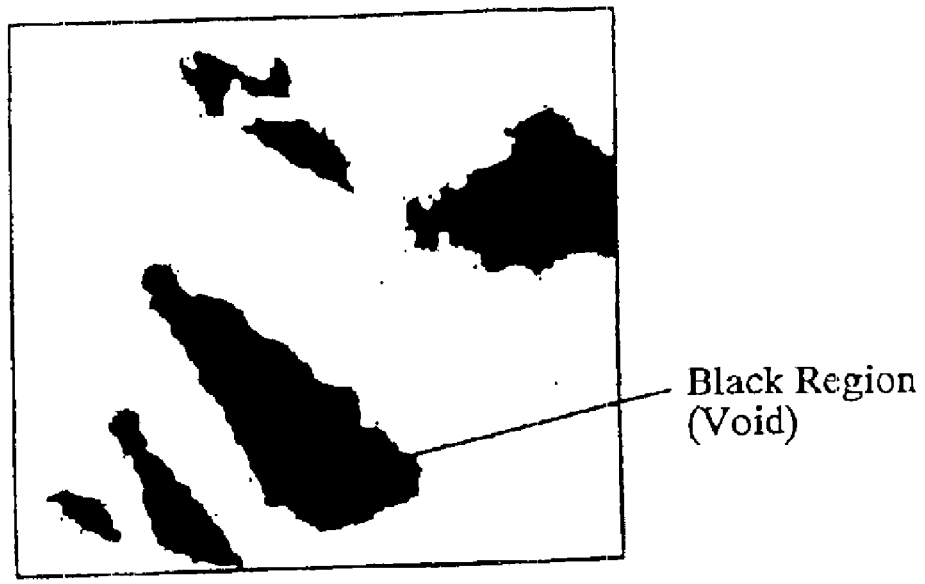
FIG. 12 is a schematic explanatory view of FIG. 11.

A dental composite material was prepared by using the resulting white powder as an ion-releasable filler, and using the same polymerizable base material A, filler A and filler B as those in Example 19 in the same composition. The same tests as those in Example 19 were conducted using the resulting filler and dental composite material. These test results are shown in Table 6. In addition, the electron microphotograph of the surface of the dental composite material after the acid resistance test is shown in FIG. 11.

TABLE 6

| | Filler | | Dental Composite Material | | | |
|---|---|---|---|---|---|---|
| | | | Amount | | Compressive | |
| | | Refractive | of Ions | | Strength (MPa) | |
| | | Index | Released | Acid | | After 10000 |
| | Transparency | ($nD^{25}$) | ($\mu g/cm^2$) | Resistance | At Start | Thermal Cycles |
| Example 18 | Excellent | 1.458 | 89 | Excellent | 423 | 407 |
| Comp. Example 6 | Poor | 1.453 | 34 | Poor | 390 | 356 |
| Example 19 | Excellent | 1.451 | 280 | Excellent | 456 | 435 |

TABLE 6-continued

| | | Dental Composite Material | | | | |
|---|---|---|---|---|---|---|
| | Filler | | Amount | | Compressive | |
| | | Refractive | of Ions | | Strength (MPa) | |
| | Transparency | Index (nD$^{25}$) | Released (μg/cm$^2$) | Acid Resistance | At Start | After 10000 Thermal Cycles |
| Comp. Example 7 | Poor | 1.450 | 120 | Poor | 421 | 385 |

Both of Examples 18 and 19 are fillers of the present invention comprising SiO$_2$ and NaF, wherein the filler has a structure such that NaF is dispersed in a matrix comprising SiO$_2$ on a very fine level of 0.3 μm or less. On the other hand, Comparative Examples 6 and 7 are fillers prepared from SiO$_2$ and fine powders of NaF, wherein the fine NaF powder used does not seem to be uniformly dispersed in the matrix comprising SiO$_2$, but partly aggregated.

As shown in Table 6, the fillers of the present invention obtained in Examples 18 and 19 had excellent transparency, and an inner portion of the particles of the filler was substantially optically uniform. However, in Comparative Examples 6 and 7, the uniformity of the inner portion of the particles of the filler was notably lower. This is thought to be due to the fact that the particle size of NaF in the inner portion of the filler is large, so that light is scattered in the inner portion. Similarly, in the acid resistance test for the polished surface, it was observed that the particles of NaF were dissolved, so that many large voids were generated on the surface of the filler in cases of Comparative Examples 6 and 7.

INDUSTRIAL APPLICABILITY

According to the present invention, there can be obtained a filler which has high water (acid) resistance against the dental composite material and high releasing functions of fluorine ions and other ions, and further is suitably used as a dental composite material which can maintain a high aesthetic appreciation of the composite material for a long period of time, and a dental composite material comprising the filler, excellent in physical durability, ion-releasability and aesthetic appreciation.

What is claimed is:

1. A filler comprising at least one metal oxide and at least one water-soluble metal salt, the metal oxide and the water-soluble metal salt each forming an independent phase, characterized in that the water-soluble metal salt phase comprises a crystal of the water-soluble metal salt having an average particle size of from 0.001 to 0.3 μm.

2. The filler according to claim 1, wherein a number ratio of crystals having a particle size of 0.3 μm or more is 20% or less of the crystals of the water-soluble metal salts.

3. The filler according to claim 1 or 2, wherein a content of the metal oxide is from 60 to 95% by mol, and a content of the water-soluble metal salt is from 5 to 40% by mol.

4. The filler according to claim 1 or 2, wherein the metal oxide is at least one compound selected from the group consisting of silicon dioxide, boron oxide, aluminum oxide, titanium oxide, zinc oxide, strontium oxide, yttrium oxide, zirconium oxide, barium oxide, lanthanum oxide and ytterbium oxide.

5. The filler according to claim 4, wherein the metal oxide comprises at least silicon dioxide.

6. The filler according to claim 1 or 2, wherein the water-soluble metal salt is:

(i) a fluorine compound; and/or (ii) at least one compound selected from the group consisting of alkali metal phosphates, alkaline earth metal phosphates, alkali metal carbonates, alkaline earth metal carbonates, alkali metal chlorides and alkaline earth metal chlorides.

7. The filler according to claim 6, wherein the fluorine compound is sodium fluoride.

8. The filler according to claim 1 or 2, wherein the photorefractive index is from 1.4 to 1.7.

9. The filler according to claim 1 or 2, which is a dental filler.

10. A process for preparing the filler according to claim 1 or 2, comprising mixing a metal oxide and/or a hydrolyzed product of a hydrolysable organometallic compound with an aqueous solution of a water-soluble metal salt, and drying the resulting mixture.

11. The process according to claim 10, wherein the mixture is a water-containing gel.

12. A dental composite material comprising the filler (a) of claim 9, a polymerizable monomer (b) and a polymerization initiator (c).

13. The dental composite material according to claim 12, wherein a content of the filler (a) is from 1 to 90% by weight.

* * * * *